US006541213B1

(12) United States Patent
Weigl et al.

(10) Patent No.: US 6,541,213 B1
(45) Date of Patent: *Apr. 1, 2003

(54) MICROSCALE DIFFUSION IMMUNOASSAY

(75) Inventors: Bernhard H. Weigl, Seattle, WA (US); Paul Yager, Seattle, WA (US); Andrew Kamholz, Seattle, WA (US); Anson Hatch, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/574,797

(22) Filed: May 19, 2000

Related U.S. Application Data

(63) Continuation-in-part of application No. 09/503,563, filed on Feb. 14, 2000, which is a continuation of application No. 09/426,683, filed on Oct. 25, 1999, now abandoned, which is a continuation of application No. 08/829,679, filed on Mar. 31, 1997, now Pat. No. 5,972,710, which is a continuation-in-part of application No. 08/625,808, filed on Mar. 29, 1996, now Pat. No. 5,716,852.

(60) Provisional application No. 60/135,417, filed on May 21, 1999.

(51) Int. Cl.$^7$ ............................................. G01N 33/533

(52) U.S. Cl. ........................... 435/7.1; 436/52; 436/53; 436/514; 436/518; 436/172; 436/177; 436/180; 422/81; 422/82; 422/82.08; 210/85; 210/94; 210/96.1; 210/511; 210/634; 210/739; 210/745; 210/748; 210/198.2; 210/243

(58) Field of Search ......................... 436/52, 53, 518, 436/172, 177, 180, 514; 422/81, 82, 82.08; 210/85, 94, 96.1, 511, 654, 739, 745, 748, 198.2, 243, 805; 435/7.1

(56) References Cited

U.S. PATENT DOCUMENTS 3,449,938 A   6/1969   Giddings ....................... 73/23

(List continued on next page.)

FOREIGN PATENT DOCUMENTS

EP   0 294 701 B1   12/1988   .......... G01N/15/14

(List continued on next page.)

OTHER PUBLICATIONS

U.S. patent application Ser. No. 09/464,379, filed Dec. 15, 1999.

(List continued on next page.)

*Primary Examiner*—Christopher L. Chin
*Assistant Examiner*—Pensee T. Do

(57) ABSTRACT

Methods and apparatuses are provided for determining presence and concentration of analytes by exploiting molecular binding reactions and differential diffusion rates. Analyte particles and binding particles are allowed to diffuse toward each other, and slowing of the diffusion front is detected when they meet. From the position of the diffusion front, presence and concentration of analyte particles can be determined. One embodiment provides a competitive immunoassay in a microfluidic format. This diffusion immunoassay (DIA) relies on measuring the concentration of labeled antigen along one dimension of a microchannel after allowing it to diffuse for a short time into a region containing specific antibodies. A simple microfluidic device, the T-Sensor, was used to implement a DIA to measure the concentration of phenytoin, a small drug molecule. Concentrations of analyte over the range of 50 to 1600 nM can be measured in less than a minute. The assay is homogeneous, rapid, requires only microliter volumes of reagents and sample, and is applicable to a wide range of analytes, including therapeutic drugs, molecular biological markers, and environmental contaminants. Methods for separating particles of similar size in a diffusion separator are also provided.

24 Claims, 10 Drawing Sheets

U.S. PATENT DOCUMENTS

| | | | |
|---|---|---|---|
| 3,795,489 A | 3/1974 | Warnick et al. | 23/254 R |
| 4,147,621 A | 4/1979 | Giddings | 210/22 C |
| 4,214,981 A | 7/1980 | Giddings | 209/155 |
| 4,250,026 A | 2/1981 | Giddings et al. | 209/155 |
| 4,683,212 A | 7/1987 | Uffenheimer | 436/52 |
| 4,726,929 A | 2/1988 | Gropper et al. | 422/68 |
| 4,737,268 A | 4/1988 | Giddings | 209/12 |
| 4,756,884 A | 7/1988 | Hillman et al. | 422/73 |
| 4,830,756 A | 5/1989 | Giddings | 210/739 |
| 4,849,340 A | 7/1989 | Oberhardt | 435/13 |
| 4,894,146 A | 1/1990 | Giddings | 209/12 |
| 4,908,112 A | 3/1990 | Pace | 204/299 |
| 5,007,732 A | 4/1991 | Ohki et al. | 356/73 |
| 5,039,426 A | 8/1991 | Giddings | 210/695 |
| 5,141,651 A | 8/1992 | Giddings | 210/748 |
| 5,156,039 A | 10/1992 | Giddings | 73/1 R |
| 5,193,688 A | 3/1993 | Giddings | 209/155 |
| 5,240,618 A | 8/1993 | Caldwell et al. | 210/748 |
| 5,250,263 A | 10/1993 | Manz | 422/81 |
| 5,288,463 A | 2/1994 | Chemelli | 422/58 |
| 5,304,487 A | 4/1994 | Wilding et al. | 435/13 |
| 5,389,524 A | 2/1995 | Larsen et al. | 435/29 |
| 5,439,578 A | 8/1995 | Dovichi et al. | 204/299 R |
| 5,465,849 A | 11/1995 | Wada et al. | 209/214 |
| 5,480,614 A | 1/1996 | Kamahori | 422/70 |
| 5,599,432 A | 2/1997 | Manz et al. | 204/451 |
| 5,599,503 A | 2/1997 | Manz et al. | 422/82.05 |
| 5,635,358 A | 6/1997 | Wilding et al. | 435/7.2 |
| 5,637,469 A | 6/1997 | Wilding et al. | 435/7.21 |
| 5,716,852 A * | 2/1998 | Yager et al. | |
| 5,726,404 A | 3/1998 | Brody | 200/81 R |
| 5,726,751 A | 3/1998 | Altendorf et al. | 356/246 |
| 5,747,349 A | 5/1998 | van den Engh et al. | 436/172 |
| 5,748,827 A | 5/1998 | Holl et al. | 385/134 |
| 5,922,210 A | 7/1999 | Brody et al. | 210/767 |
| 5,932,100 A * | 8/1999 | Yager et al. | |
| 5,942,443 A | 8/1999 | Parce et al. | 436/514 |
| 5,948,684 A * | 9/1999 | Weigl et al. | |
| 5,971,158 A * | 10/1999 | Yager et al. | |
| 5,972,710 A * | 10/1999 | Weigl et al. | |
| 5,974,867 A | 11/1999 | Forster et al. | 73/61.41 |
| 6,067,157 A | 5/2000 | Altendorf | 356/337 |
| 6,136,272 A | 10/2000 | Weigl et al. | 422/82.05 |
| 6,221,677 B1 * | 4/2001 | Wu et al. | |

FOREIGN PATENT DOCUMENTS

| | | | |
|---|---|---|---|
| EP | 0 381 501 A2 | 8/1990 | B01L/3/00 |
| EP | 0 645 169 A1 | 3/1995 | B01D/21/00 |
| WO | WO 93/22053 | 11/1993 | H01L/3/00 |
| WO | WO 96/04547 | 2/1996 | G01N/27/00 |
| WO | WO 96/12541 | 5/1996 | B01D/11/04 |
| WO | WO 96/15576 | 5/1996 | H92K/44/02 |
| WO | WO 97/00125 | 1/1997 | B01F/5/06 |
| WO | WO 97/02357 | 1/1997 | C12P/19/34 |
| WO | WO 98/43066 | 10/1998 | G01N/15/14 |
| WO | WO 99/17100 | 4/1999 | G01N/21/64 |
| WO | WO 99/17119 | 4/1999 | G01N/33/543 |
| WO | WO 99/60397 | 11/1999 | G01N/33/483 |

OTHER PUBLICATIONS

U.S. patent application Ser. No. 09/404,454, filed Sep. 22, 1999.

U.S. patent application Ser. No. 09/346,852, filed Jul. 2, 1999.

U.S. patent application Ser. No. 09/196,473, filed Nov. 19, 1998.

U.S. patent application Ser. No. 09/169,533, filed Oct. 9, 1998.

U.S. patent application Ser. No. 09/724,308, filed Nov. 28, 2000.

Booker, H.E. and Darcey, B.A. (1975) "Enzymatic Immunoassay vs Gas/Liquid Chromatography for Determination of Phenobarbital and Diphenylhydantoin in Serum," *Clin. Chem.* 21:1766–1768.

Brody, J.P. and P. Yager, (1997) "Diffusion–based extraction in a microfabricated device," *Sensors and Actuators A (Physical)* A58(1):13–18.

Brody, J.P. and Yager, P. (Jun. 1996), "Low Reynolds Number Micro–Fluidic Device," *Solid State Sensor & Actuator Workshop Hilton Head,* SC, Jun. 2–6, pp. 105–108.

Brody et al., (Dec. 1996) "Biotechnology at Low Reynolds Numbers," *Biophysical Journal* 71:3430–3441.

Chiem, N. and D.J. Harrison, (Feb. 1997) "Microchip–Based Capillary Electrophoresis for Immunoassays: Analysis of Monoclonal Antibodies," *Anal. Chem.* 69:373–378.

Chmelik, Josef (1991), "Isoelectric focusing field–flow fractionation," *J. Chromatography* 545(2) 349–358.

Darling et al., (Oct. 1998) "Integration of microelectrodes with etched microchannels for in–stream electrochemical analysis," μTAS '98, Banff, Canada pp. 105–108.

de Alwis, U. and G. S. Wilson, (1987) "Rapid Heterogeneous Competitive Electrochemical Immunoassay for IgG in the Picomole Range," *Anal. Chem.* 59:2786–2789.

Ekins, R. (1994) "Immunoassay: recent developments and future directions," *Nuclear Medicine and Biology* 21:495–521.

Faucheux, L.P. et al. (Feb. 1995), "Optical Thermal Ratchet," *Phys. Rev. Letters* 74:1504–1507.

Fuh et al., (1993) "Rapid Diffusion Coefficient Measurements Using Analytical SPLITT Fractionation: Applicaton to Proteins,"*Anal. Biochem.* 208:80–87.

Giddings, J.C. (1985), "Optimized Field–Flow Fractionation System and Based on Dual Stream Splitters." *Anal. Chem.* 57:945–947.

Giddings, J.C. et al. (1983), "Outlet Stream Splitting for Sample Concentration in Field–Flow Fractionation," *Separation Science & Technology* 18:293–306.

Giddings, J.C. (1993) "Field–Flow Fractionation: Analysis of Macromolecular, Colloidal and Particulate Materials," *Science* 260:1456–1465.

Griffiths et al., (1993) "Human anti–self antibodies with high specificity from phage display libraries," *EMBO J.* 12:725–734.

Hicks, J.M., (1984) "Fluorescence Immunoassay," *Human Pathology* 15:112–116.

Kamholz et al., (Dec. 1999) "Quantitative Analysis of Molecular Interaction in a Microfluidic Channel: The T–Sensor," *Anal. Chem.,* 71(23):5340–5347.

Leff, H.S. and Rex, A.F. (1990), "Resource letter MD–1: Maxwell's demon," *Am. J. Physics* 58:201–209.

Manz, A. et al. (1993), "Planar chips technology for miniaturization of separation systems: A developing perspective in chemical monitoring," *Advances in Chromatography* 33:2–66.

McGregor et al. (1978) "Polarisation Fluoroimmunoassay of Phenytoin," *Clin. Chim. Acta* 83:161–166.

Montgomery et al. (1975), "Determination of Diphenylhydantoin in Human Serum by Spin Immunoassay," *Clin. chem.* 21:221–226.

Paxton, J.W. et al. (1976) "Production and Characterisation of Antisera to Diphenylhydantoin Suitable for Radioimmunoassay," *J. Immunol. Methods* 10:317–327.

Petersen, K.E. (1982), "Silicon as a Mechanical Material," *Proc. IEEE 70(5)*:420–457.

Porstmann, T. and Kiessig, S.T.(1992) "Enzyme immunoassay techniques," *J. Immunol. Methods 150:*5–21.

Reisman, A. et al. (1979) "The Controlled Etching of Silicon in Catalyzed Ethylenediamine–Pyrocatechol–Water Solutions," *J. Electrochem. Soc. 126:*1406–1415.

Rousselet, J. et al. (1994), "Directional motion of brownian particles induced by a periodic asymmetric potential," *Nature 370:*446–448.

Shoji, S. and Esashi, M. (1994), "Microflow devices and systems," *J. Micromechanics and Microengineering 4:*157–171.

Verpoorte, E.M.J. et al. (1994), "Three–dimensional micro flow manifolds for miniaturized chemical analysis systems," *J. Micromech. Microeng. 4*:246–256.

Wallis, G. and Pomerantz, D.I. (1969) "Field Assisted Glass–Metal Sealing," *J. Appl. Physics 40:*3946–3949.

Weigl, B.H. and P. Yager, (Jan. 1999) "Microfluidic Diffusion–Based Separation and Detection," *Science 283:*346–347.

Weigl et al., (Oct. 1998) "Simultaneous self–referencing analyte determination in complex sample solutions using microfabricated flow structures (T–Sensors)," *μTAS '98*, Banff, Canada.

Weigl, B.H. et al. (Feb. 1997), "Fluorescence and absorbance analyte sensing in whole blood and plasma based on diffusion separation in silicon–microfabricated flow structures," SPIE Proceedings, J. Lakowitz (ed.) *Fluorescence Sensing Technology III* (Feb. 9–11).

Weigl, B.H. and Yager, P. (Apr. 1996), "Silicon–Microfabricated Diffusion–Based Optical Chemical Sensor," presented at Europtrode Conference, Zurich, Switzerland, Apr. 2–3.

Weigl, B.H. et al. (Nov. 1996), "Rapid sequential chemical analysis in microfabricated flow structures using multiple fluorescent reporter beads," *μ*TAS 96 (Nov'96).

Weigl et al., (Nov. 1996) "Diffusion–Based Optical Chemical Detection in Silicon Flow Structures," *Anal. Methods & Instr.,* 174–184.

Weigl, B.H. and P. Yager, (Mar./Apr. 1996) "Silicon–microfabricated diffuusion–based optical chemical sensor," *Sensors and Actuators B (Clinical) B39 (1–3)*, 452–457.

Williams, P.S. et al. (1992), "Continuous SPLITT Fractionation Based on a Diffusion Mechanism," *Ind. Eng. Chem. Res. 31:*2172–2181.

* cited by examiner

MICROSCALE DIFFUSION IMMUNOASSAY

CROSS-REFERENCE TO RELATED APPLICATIONS

This application is a continuation-in-part of U.S. application Ser. No. 09/503,563 filed Feb. 14, 2000, which claims priority from U.S. Provisional Application No. 60/135,417 filed May 21, 1999. This application is a continuation of U.S. application Ser. No. 09/426,683 filed Oct. 25, 1999, now abandoned which is a continuation of U.S. application Ser. No. 08/829,679 filed Mar. 31, 1997, now U.S. Pat. No. 5,972,710, which is a continuation-in-part of U.S. application Ser. No. 08/625,808 filed Mar. 29, 1996, now U.S. Pat. No. 5,716,852. All of the foregoing applications are incorporated by reference herein to the extent not inconsistent herewith.

BACKGROUND OF THE INVENTION

The immunoassay is the workhorse of analytical biochemistry. It allows the unique binding abilities of antibodies to be widely used in selective and sensitive measurement of small and large molecular analytes in complex samples. The driving force behind developing new immunological assays is the constant need for simpler, more rapid, and less expensive ways to analyze the components of complex sample mixtures. Current uses of immunoassays include therapeutic drug monitoring, screening for disease or infection with molecular markers, screening for toxic substances and illicit drugs, and monitoring for environmental contaminants.

Flow injection immunoassays have taken advantage of specific flow conditions. (U. de Alwis and G. S. Wilson, *Anal. Chem.* 59, 2786–9 (1987)), but also use high Reynolds number effects for mixing. Micro-fabricated capillary electrophoresis devices, which are truly microfluidic, have been used for rapidly separating very small volumes of immunoreagents following binding reactions (N. Chiem and D. J. Harrison, *Anal. Chem.* 69, 373–8 (1997)). One of the unique features of microfluidic devices that has yet to be exploited for immunoassay development is the presence of laminar flow under low Reynolds number conditions. Laminar flow allows quantitative diffusional transport between adjacent flowing streams, while retaining the relative positions of non-diffusing components such as cells and larger microspheres. While these conditions are impediments to application of some macro-scale techniques, they allow creation of new types of analyses that are uniquely well suited to microfluidic systems, such as the H-Filter for extraction of solutes (J. P. Brody, P. Yager, R. E. Goldstein, R. H. Austin, *Biophysical Journal* 71(6), 3430–3441 (1996); U.S. Pat. No. 5,932,100; J. P. Brody and P. Yager, *Sensors and Actuators A (Physical)* A58(1), 13–18 (1997); the V-Groove device for low-volume flow cytometry; U.S. Pat. No. 5,726,751, the T-Sensor for detection of diffusable analytes (A. E. Kamholz, B. H. Weigl, B. A. Finlayson, P. Yager, [1999] *Anal. Chem.*, 71(23):5340–5347; U.S. Pat. No. 5,716,852; U.S. Pat. No. 5,972,710; B. H. Weigl and P. Yager, *Science* 283, 346–347 [1999]; R. B. Darling, J. Kriebel, K. J. Mayes, B. H. Weigl, P. Yager, Integration of microelectrodes with etched microchannels for in-stream electrochemical analysis, µTAS '98, Banff, Canada [1998]; B. H. Weigl and P. Yager, *Sensors and Actuators B (Chemical)* B39 (1–3), 452–457 [1996]; B. H. Weigl, M. A. Holl, D. Schutte, J. P. Brody, P. Yager, *Anal. Methods & Instr.*, 174–184 [1996]; B. H. Weigl, et al., Simultaneous self-referencing analyte determination in complex sample solutions using microfabricated flow structures (T-Sensors), µTAS '98, Banff, Canada [1998]) and others as described in U.S. Pat. No. 5,922,210; U.S. Pat. No. 5,747,349; U.S. Pat. No. 5,748,827; U.S. Pat. No. 5,726,404; U.S. Pat. No. 5,971,158; U.S. Pat. No. 5,974,867 and U.S. Pat. No. 5,948,684; WO 98/43066 published Oct. 1, 1998; U.S. Ser. No. 08/938,584 filed Sep. 26, 1997; WO 99/17100 published Apr. 8, 1999; WO 99/17119 published Apr. 8, 1999; U.S. Ser. No. 09/196,473 filed Nov. 19, 1998; U.S. Ser. No. 09/169,533 filed Oct. 9, 1998; WO 99/60397 published Nov. 25, 1999; U.S. Ser. No. 09/404,454 filed Sep. 22, 1999; and Ser. No. 09/464,379, filed Dec. 15, 1999 for "Magnetically-Actuated Fluid Handling Devices for Microfluidic Applications."

All publications referred to herein are hereby incorporated by reference in their entirety to the extent not inconsistent herewith.

SUMMARY

This invention provides a method for detecting the presence of analyte particles comprising providing binding particles capable of binding with said analyte particles; providing a system in which at least one of said binding particles and said analyte particles can diffuse toward the other; providing means for detecting any of said particles or complexes between them, or a diffusion front of said binding particles, said analyte particles, or said complexes in said system, and detecting said particles or complexes or said diffusion front. When said analyte particles and said binding particles meet and bind to each other, a slowing of the particles or a diffusion front may be detected as an indication of the presence of said analyte particles. The binding particles, or the analyte particles, or complexes between them must be visible or detectable, e.g. by optical or electrical detection means or other detection means known to the art, or must be labeled to become visible or detectable.

This invention also provides a device for determining the presence or concentration of sample analyte particles in a medium comprising: means for contacting a first medium containing analyte particles with a second medium containing binding particles capable of binding to said analyte particles; wherein at least one of said analyte or binding particles is capable of diffusing into the medium containing the other of said analyte or binding particles; and means for detecting the presence of diffused particles. One or both of the analyte and binding particles may be labeled or unlabeled.

The "diffusion front" (also referred to as "diffusion profile" herein) is a detectable edge or line created by diffusing particles. It may be more or less sharp or diffuse depending on system parameters such as relative amounts of analyte and binding particles, relative diffusion coefficients of both, amount of labeling, viscosities of the system, and other parameters known to the art. The term "slowing" with reference to the diffusion front includes stopping, as well as any detectable amount of slowing. The "diffusion front" may include a detectably more intense area or line closer to the point(s) from which diffusion of particles begins caused by complexing of labeled particles to form slower-diffusing complexes, with relatively less intense areas further from said points caused by uncomplexed labeled particles; or the "diffusion front" may be the absolute border of the area into which particles have diffused.

Systems allowing diffusion of analyte or binding particles toward each other can be systems in which fluids containing analyte particles (referred to herein as analyte fluids) are placed in contact with fluids containing binding particles (referred to herein as "diffusion fluids"), or fluids containing analyte particles, are placed in contact with solids containing binding particles capable of diffusing into the analyte fluid. Or, the system may be one in which fluids containing binding particles are placed in contact with solids containing analyte particles capable of diffusing into the diffusion fluids. Such systems can be flowing or stationary systems as described below, or can comprise fluids separated by membranes capable of allowing diffusion of analyte and/or binding particles therethrough, or can comprise two fluids containing analyte and binding particles respectively separated by a removable barrier, which is removed to allow diffusion to take place.

Slowing of the diffusion front may be observed or detected; or the position of the diffusion front after a predetermined time from when the particles begin diffusing may be observed or otherwise detected and compared with a similar calibration or control system or systems containing known amounts of analyte particles, e.g. from 0 to any typical concentration. In this way, concentration as well as presence of analyte particles can be determined.

Concentration may also be calculated based on the principles and algorithms described in the Examples below, and determinable without undue experimentation by those skilled in the art.

This invention also provides methods for detecting the presence of at least first and second analyte particles in a first fluid comprising: providing a second fluid comprising first and second binding particles for said first and second analyte particles, respectively; flowing said first and second fluids in adjacent laminar flow in a laminar flow channel; allowing said first analyte particles to diffuse into said second fluid and bind with said first binding particles to form first complexes; and allowing said second analyte particles to diffuse into said second fluid and bind with said second binding particles to form second complexes; and detecting the presence of said first and second complexes. The first and second complexes may have detectably different diffusion coefficients and/or may form detectably different diffusion profiles, e.g. because the diffusion front for each is in a different position, or because the first and second complexes are differently labeled. The first and second complexes may or may not labeled with detectably different labels. If detectably different labels are not used, different diffusion coefficients of the two complexes may enable them to be drawn out of the laminar flow channel at different points, in separate outlet streams, each comprising either the faster-diffusing complexes or mixtures of complexes. Diffusion separators connected in series may continue to purify and refine the separator products. The various complexes may then be detected in the separate streams by means known to the art.

Devices for detecting the presence of at least first and second analyte particles in a first fluid are also provided, comprising: first inlet means for conducting a first fluid comprising said first and second analyte particles into a laminar flow channel; second inlet means for conducting a second fluid comprising first and second binding particles for said first and second analyte particles, respectively, into said laminar flow channel; a laminar flow channel in fluid communication with said first and second inlet means, comprising said first and second fluids in adjacent laminar flow, said flow channel having a length sufficient to allow said first analyte particles to diffuse into said second fluid and bind with said first binding particles to form first complexes; and to allow said second analyte particles to diffuse into said second fluid and bind with said second binding particles to form second complexes; and means for detecting the presence of said first and second complexes. The first and second complexes may have detectably different diffusion coefficients and/or diffusion profiles, and may or may not be labeled with detectably different labels. The devices may also comprise outlet means spaced along said laminar flow channel for conducting a stream comprising said first complexes from said channel as a first outlet stream, and/or additional outlet means spaced along said laminar flow channel for conducting a stream comprising mixtures of said first and second complexes from said channel as a second outlet stream, as well as means for detecting the presence of first analyte particles in the first outlet stream and means for detecting the presence of second analyte particles in the second outlet stream.

This invention also provides a method for separating first and second particles of similar size contained in a first fluid, in a diffusion separator, said method comprising: providing a second fluid comprising at least first and second binding particles for said first and second analyte particles, respectively, said first binding particles having a higher diffusion coefficient than said second binding particles; flowing said first fluid into a channel comprising said second fluid; allowing said first analyte particles to diffuse into said second fluid and bind with said first binding particles to form first complexes; and allowing said second analyte particles to diffuse into said second fluid and bind with said second binding particles to form second complexes; conducting a stream predominantly containing said first complexes from said channel through a first outlet; and conducting a stream containing said first and second complexes from said channel through a second outlet positioned downstream from said first outlet along said channel.

The foregoing method may be performed in a diffusion separator which is a device for separating first and second particles of similar size contained in a first fluid, said device comprising: a flow channel comprising a second fluid containing at least first and second binding particles for said first and second analyte particles, respectively, said first binding particles having a higher diffusion coefficient than said second binding particles; a first inlet into said channel on a first side of said channel, said first inlet containing said first fluid; a second inlet on the second side of said flow channel containing an acceptor stream; a first outlet on the second side of said flow channel downstream from said second inlet containing a stream predominantly comprising said first complexes; and a second outlet on the second side of said flow channel downstream from said first outlet containing a stream containing said first and second complexes. The device may also comprise a third outlet on the first side of said flow channel through which unbound first and second particles may be removed from the system. An additional diffusion separator, such as the H-filter described in U.S. Pat. No. 5,932,100, may be connected to the first outlet and used to separate first complexes from unbound particles. A diffusion separator may also be connected to the second outlet and used to separate first and second complexes, and if further separation of unbound particles is required, further diffusion separators may be added.

Preferably, for the foregoing separation methods and devices, the diffusion coefficients of the first and second binding particles differ by at least two times, and preferably by at least about ten times. The particles to be separated do not need to be of identical size (diameter), but are of similar size, e.g., within the same order of magnitude.

In some embodiments of the analytical methods of this invention, analyte particles in the system may be supplemented with labeled analyte particles, and the diffusion front observed and compared with systems containing only labeled analyte particles (and no unlabeled analyte particles). Earlier and more complete slowing or stopping of the diffusion front will occur when (as a result of complexation of analyte particles with binding particles) the concentration of binding particles more greatly exceeds that of the analyte particles. However, it is not essential that binding particle concentration exceed analyte particle concentration.

The system may comprise a number of uniquely labeled binding particles, so that the unique diffusion fronts which are detected indicate which analyte particles are present.

Flowing systems, comprising preferred embodiments of this invention, are described below, and give rise to stationary diffusion profiles. The position of such stationary diffusion profiles are used to determine concentration of analyte particles.

In preferred embodiments, this invention provides a method for determining the presence or concentration of sample analyte particles in an analyte fluid comprising: adding to an analyte fluid additional analyte particles labeled with a detectable marker to provide a predetermined concentration or amount of labeled analyte particles in said analyte fluid; providing a diffusion fluid containing binding particles capable of binding to said sample analyte particles and said labeled analyte particles; providing a laminar flow channel comprising an analyte stream inlet and a diffusion stream inlet; flowing analyte fluid into said analyte stream inlet as an analyte stream, and flowing diffusion fluid into said diffusion stream inlet as a diffusion stream whereby said streams flow in adjacent laminar flow; allowing diffusion between said streams of sample analyte particles, labeled analyte particles and binding particles; detecting a diffusion profile in said channel formed by said labeled analyte particles; and determining from said diffusion profile the presence or concentration of said sample analyte particles.

Analyte particles may be molecules, preferably having a molecular weight range between about 100 and about 1,000,000, or particles of corresponding size. The terms "sample antigen" or "SA," as used herein, refer to analyte particles. Analyte particles may also be antibodies.

Analyte particles for which the present invention may be used include, but are not limited to, abused drugs such as amphetamine and methamphetamine, barbiturates, benzodiazepines, benzodiazepine in serum, cannabinoids, cocaine metabolites, ethanol, methadone, opiates, phencyclidine, propoxyphene, salicylate, tricyclic and antidepressants; cancer drugs such as methotrexate; fertility and pregnancy drugs such as free estriol, selected prolactins, and total estriol; medications for heart disease; anti-inflammatories; drugs which require therapeutic monitoring such as amikacin, carbamazepine, digitoxin, digoxin, disopyramide, ethosuximide, free carbamazepine, free phenytoin, free valproic acid, gentamicin, lidocaine, N-acetylprocainamide, netilmicin, phenobarbital, phenytoin, primidone, procainamide, quinidine, theophylline, tobramycin, valproic acid, vancomycin; endogenous molecules such as thyroid; antigens detected in assay systems such as T-Uptake, including T4; antigens used in transplant monitoring including assays of cyclosporine, serum cyclosporine, cyclosporine in whole blood, and cortisol.

The analyte fluid may be an aqueous solution containing the antigen, a bodily fluid such as whole blood, serum, saliva, urine or other fluid, contaminated drinking water, fermentation broths, samples from industrial processes requiring monitoring, or any other fluid for which analysis is required.

Detectable markers or labeling agents for labeling the analyte particles or binding particles include any particles capable of binding or adhering to the analyte particles and not interfering with binding of the binding particle selected for the assay. Labeling agents may include fluorescent, phosphorescent, chemiluminescent, enzyme particles, and other labeling agents known to the art. The terms "labeled antigen" and "LA" as used herein refer to labeled analyte particles. Labeling agents should be small enough to provide label/analyte particle complexes which are of similar size (at least in the same order of magnitude) as the unlabeled analyte particles so that diffusion coefficients of the labeled analyte particles are roughly equivalent to diffusion coefficients of unlabeled analyte particles. For example, an analyte particle having a molecular weight of 10,000 might be labeled with a molecule having a molecular weight of about 100 to 1,000. The labeling particle should not be so large as to significantly change the diffusion properties of the binding particle/labeled analyte complex as compared to the diffusion properties of the binding particle analyte complex. The label may be soluble or insoluble in the fluid and may adhere to the analyte particle by adsorption, absorption or chemical binding. For example, the labeling agent can be a conventional art-known dye, a metal particle, or any other detectable particle known to the art.

The term "particles" includes molecules, cells, large molecules such as proteins, small molecules comprised of one or several atoms, and ions. The particles may be suspended or dissolved in the streams. The term "stream" refers to a carrier fluid such as water or other liquid, air or other gas, dissolving or suspending the particles. The term "particles" as used herein does not include the molecules of the carrier stream.

The binding particle may be any particle capable of binding or adhering, e.g., by covalent or ionic binding, absorption adsorption or other means known to the art, to the analyte particle and with the labeled analyte particle to form complexes with a diffusion coefficient greater than that of the analyte particle and labeled analyte particle. Preferably the diffusion coefficient of the complex is very much greater than that of the labeled analyte particles, and should be at least about two to five times greater than that of the labeled analyte particles, more preferably at least about ten times greater than that of the labeled analyte particles. Preferably the binding particle is at least as large as the analyte particle. The binding particle may be an antibody, either monoclonal or polyclonal, or a synthetic binding particle made using a combinatorial process to provide a specific binding site, or a particle of a substance such as activated charcoal capable of adhering to the labeled analyte particle. Binding particles as defined above may also function as analyte particles, e.g., antibodies may function as analyte particles herein. Preferably the binding particle has a binding affinity to the analyte particle of at least about $10^7$ $M^{-1}$ to about $10^{10}$ $M^{-1}$ and more preferably at least about $10^8$ $M^{-1}$. Since antibodies typify a preferred class of binding particles of this invention, the terms "antibody" or "AB" as used herein also refer to "binding particles."

The diffusion fluid is a carrier fluid for the binding particles and can be any carrier fluid having a viscosity which allows diffusion of the analyte particles into the diffusion stream. In some systems, the viscosity of the diffusion fluid is between about one and about four times that of water. More viscous systems require longer times for performing the assay. The viscosities of the analyte fluid and the diffusion fluid need not be the same and can differ greatly so long as diffusion from the analyte fluid into the diffusion fluid is significant enough to allow measurement. The diffusion fluid is capable of dissolving or suspending the binding particles and the analyte particles at the flow rate used to flow the diffusion stream through the laminar flow channel.

As discussed above, both the analyte and binding particles need not be present in a fluid. One type of particle can be in solid form, so long as the other is contained in a fluid, into which the first type of particle can diffuse.

In one embodiment of this invention, a predetermined (known) amount of labeled analyte particles is added to the analyte fluid to achieve a predetermined (known) concentration of labeled analyte particles in the analyte fluid. Preferably, tracer amounts of labeled analyte particles are used, e.g., within two to three orders of magnitude less than the estimated concentration of the unlabeled analyte particles. The concentration of labeled analyte particles should be in the same dynamic range of measurement as that of the analyte particles, that is, enough to significantly compete with analyte particles for adherence to the binding particles, but not so much that the presence of unbound labeled analyte overpowers the ability to detect the diffusion profile formed by labeled analyte particle/binding particle complexes.

The term "laminar flow" of two streams means stable, side-by-side, non-recirculating, flow of two streams without mixing. There are no zones of recirculation, and turbulence is negligible. A "laminar flow channel" is a channel having dimensions, as is known to the art, allowing such non-turbulent flow under flow rates used.

As is known to the art, a field force may be exerted in the diffusion direction of the fluids to enhance the effects of diffusion and the signal to noise ratio of the detection means chosen. Such field forces include magnetic, gravitational, and electrical fields.

Certain embodiments of the methods of this invention are designed to be carried out in devices comprising microchannels of a size such that the Reynolds number for flow within the channel is below about 1. Reynolds number is the ratio of inertia to viscosity. Low Reynolds number means that inertia is essentially negligible, turbulence is essentially negligible, and the flow of the two adjacent streams is laminar, i.e., the streams do not mix except for the diffusion of particles as described above.

In this patent application, the distance in the flow direction of the laminar flow channel from the entrance of the channel to the detection area is called its length (l). Referring to FIG. 2A, l is measured from the middle of analyte stream inlet 16 to detection zone 26. The channel dimension in the direction of particle diffusion at right angles to the length (l) is called its depth (d). The third channel dimension at right angles to both the length and depth is called its width (w). The depth (d) is therefore perpendicular to the plane of interface of the sample and extraction streams The laminar flow channel may include inlets and outlets along its length to provide reference or other reagent streams, or conduct separate streams away from the channel for analysis, disposal, or further processing. The devices of this invention may also include inlets for reference and control streams as described in U.S. Pat. No. 5,948,684.

The analyte stream inlet and the diffusion stream inlet need only be sized large enough to conduct the analyte and diffusion streams into parallel laminar flow, e.g., may comprise channels less than or equal to about 5 mm in length, less than about 100 micrometers in depth and less than or equal to about 5 mm in width, preferably less than about 1 mm in width. These inlets may be as long, deep and wide as required by the system of which they are a part, however, they preferably have a volume less than about 2.5 microliters to accommodate small sample sizes.

The width and depth of the laminar flow channel and inlet and outlet channels must be large enough to allow passage of the particles and is preferably between about 3 to 5 times the diameter of any particles present in the streams and less than or equal to 5 mm. The width is preferably less than or equal to 1 mm.

In a second embodiment in which the particle transport direction may be rotated 90 degrees from that of the "T" design shown in FIG. 2, the laminar flow channel is preferably between about 3 and 5 times the diameter of maximum-sized particles and less than or equal to 5 mm in width, between about 2 and 3 times the diameter of the maximum-sized particles and less than about 100 micrometers in depth, and between about 4 and about 10 times the diameter of the maximum-sized particles and less than or equal to 5 mm long.

The term "aspect ratio" as used herein refers to the ratio of the width to the depth of a channel. The extraction channels of this invention may have an aspect ratio less than 50, e.g., the aspect ratio may be less than 25 or any number from less than 1 to 49.

Means for injecting the analyte and diffusion streams into the device are provided, and include standard syringes and tubes. Means for removing fluid from the outlet(s) may also be provided, including receptacles for the fluid, inducing flow by capillary attraction, pressure, gravity, and other means known to the art as described above. Such receptacles may be part of an analytical or other device for further processing the streams or portions thereof.

The detectable diffusion profile of the flowing microchannel embodiments of this invention is the spatial location of labeled analyte particles within the reference area. The diffusion profile for a given concentration of analyte particles stays the same over time in these systems as long as the flow speed is constant, when dynamic equilibrium has been reached. The diffusion profile can be varied by varying flow rate, analyte concentration, and/or binding particle concentration so as to optimize the signal for detection.

The detection area is the portion of the laminar flow channel where the diffusion profile is interrogated by the detection means. It should be far enough from the junction of the two streams for significant reaction between binding particles and analyte particles to have occurred. However, it should not be so far along the channel that the particles have spread apart enough to significantly diminish signal intensity. The detection area, i.e., the length (l) from the junction of the analyte and diffusion fluids to the point where the diffusion profile is detected, can be optimized in accordance with these principles to optimize signal-to-noise ratio.

The step of allowing the particles to diffuse includes allowing the analyte and diffusion streams to be in contact for a sufficient period of time to form a stable diffusion profile at the detection area.

The length of the laminar flow channel is long enough to permit small analyte particles and labeled analyte particles to diffuse from the analyte stream and bind to the binding particles and can vary from several microns to 50 mm or more, depending on the sensitivity and size of the detection means, the pump capacities and flow rates and volumes, and diffusion of the particles. Flow rates may be adjusted to be fast enough to prevent particles from settling. Flow rates can vary as required, e.g., between about 5 $\mu$m/sec to about 5000 $\mu$m/sec.

The methods of this invention may be performed using reference and/or control streams in laminar flow in the laminar flow channel with the analyte and diffusion streams. For example, a reference stream containing a known concentration of analyte particles and labeled analyte particles may be flowed into the laminar flow channel adjacent to the diffusion stream so that the diffusion profile of the analyte stream into the diffusion stream may be directly compared with the diffusion profile of the reference stream into the diffusion stream.

The term "microfabricated" refers to devices having dimensions such that flow therein is substantially laminar. Preferably the width (dimension orthogonal to the diffusion direction and the flow direction) of the channels is less than about 1 mm.

The devices of this invention can be fabricated from any moldable, machinable or etchable material such as glass, plastic, or silicon wafers. Substrate materials which are optically transparent for a given wavelength range allow for optical detection in that wavelength range, e.g., absorbance or fluorescence measurements, by transmission. Alternatively, substrate materials which are reflective allow for optical detection by reflection. Substrate materials do not have to allow for optical detection because other art-known methods of detection are suitable as well. Non-optical detection methods include electrochemical detection and conductivity detection.

The term "machining" as used herein includes printing, stamping, cutting and laser ablating. The devices can be formed in a single sheet, in a pair of sheets sandwiched together, or in a plurality of sheets laminated together. The term "sheet" refers to any solid substrate, flexible or otherwise. The channels can be etched in a silicon substrate and covered with a cover sheet, which can be a transparent cover sheet. In a laminated embodiment, the channel walls are defined by removing material from a first sheet and the channel top and bottom are defined by laminating second and third sheets on either side of the first sheet. Any of the layers can contain fluid channels. In some cases the channel is simply a hole (or fluid via) to route the fluid to the next fluid laminate layer. Any two adjacent laminate layers may be permanently bonded together to form a more complex single part. Often fluidic elements that have been illustrated in two separate layers can be formed in a single layer.

Each layer of a laminate assembly can be formed of a different material. The layers are preferably fabricated from substantially rigid materials. A substantially rigid material is inelastic, preferably having a modulus of elasticity less than 1,000,000 psi, and more preferably less than 600,000 psi. Substantially rigid materials can still exhibit dramatic flexibility when produced in thin films. Examples of substantially rigid plastics include cellulose acetate, polycarbonate, methylmethacrylate and polyester. Metals and metal alloys are also substantially rigid. Examples include steels, aluminum, copper, etc. Glasses, silicon and ceramics are also substantially rigid.

To create the fluidic element in the sheets, material may be removed to define the desired structure. The sheets can be machined using a laser to ablate the material from the channels. The material can be removed by traditional die cutting methods. For some materials chemical etching can be used. Alternatively, the negative of the structure desired can be manufactured as a mold and the structure can be produced by injection molding, vacuum thermoforming, pressure-assisted thermoforming or coining techniques.

The individual layers, assemblies of layers, or molded equivalents may be bonded together using adhesives or welding. Alternatively, the layers may be self-sealing or mechanical compression through the use of fasteners such as screws, rivets and snap-together assembly can be used to seal adjacent layers. Layers can be assembled using adhesives in the following ways. A rigid contact adhesive (for example, 3M1151) can be used to join adjacent layers. A solvent release adhesive may be used to chemically bond two adjacent players. An ultraviolet curing adhesive (for example, Loctite 3107) can be used to join adjacent layers when at least one layer is transparent in the ultraviolet. Precision applied epoxies, thermoset adhesives, and thermoplastic adhesives can also be used. Dry coatings that can be activated to bond using solvents, heat or mechanical compression can be applied to one or both surfaces. Layers can be welded together. For welding the layers preferably have similar glass transition temperatures and have mutual wetting and solubility characteristics. Layers can be welded using radio frequency dielectric heating, ultrasonic heating or local thermal heating.

The laminar flow channel can be straight or convoluted in any of a number of ways. In one embodiment, the flow channel can include a series of turns, making a stairstep or square wave geometry. Convoluted channels provide longer distances for diffusion to occur without increasing the size of the substrate plate in which the channel is formed.

The devices of this invention may comprise detecting means external to the channel for detecting the diffusion profile. Detection and analysis is done by any means known to the art, including optical means, such as optical spectroscopy, light scattering, and other means such as absorption spectroscopy or fluorescence, electrical means, e.g. electrodes inserted into the device, or virtually any microanalytical technique known to the art including magnetic resonance techniques, or other means known to the art to detect the diffusion profile. Preferably optical, fluorescent or chemiluminescent means are used. More preferably the labels used for the analyte particles are fluorescent and detection is done by means of a CCD camera or a scanning laser with a photomultiplier.

Computer processor means may be used to determine the presence or concentration of the analyte particles from the detected diffusion profile. The processor may be programmed to compare the diffusion profile with diffusion profiles taken using varying known concentrations of analyte, e.g., calibration curves or diffusion profiles in reference streams or to calculate analyte concentrations using algorithms described below.

The diffusion immunoassay method of this invention may be practiced as a continuous flow process, continuously monitoring analyte presence and/or concentration in a stream, or may be practiced in batch mode using small sample aliquots.

The concentration of binding particles in the diffusion fluid is preferably greater than or equal to the concentration of analyte particles in the analyte fluid, e.g. at least about one to about ten times greater. The analyte particles preferably encounter more binding particles than required. This can be adjusted to occur using flow rates and/or concentrations. High flow rates of the diffusion fluid will produce a narrower detectable band, and fewer binding particles are required.

The methods of this invention also include a non-flowing method of determining the presence or concentration of sample analyte particles in an analyte substance comprising: adding to an analyte substance additional analyte particles labeled with a detectable marker to provide a predetermined concentration of labeled analyte particles in said analyte substance; providing a diffusion substance containing binding particles capable of binding to said sample analyte particles and said labeled analyte particles; contacting said analyte substance with said diffusion substance; allowing diffusion of sample analyte particles and labeled analyte particles between said analyte and diffusion substances; detecting a diffusion profile formed by said labeled analyte particles; and determining from said diffusion profile the presence or concentration of said sample analyte particles.

The foregoing method is a non-flowing system in which it is not necessary that the substances containing the analyte particles and the binding particles be in parallel laminar flow. All that is required that they be in contact for a sufficient period of time to form a diffusion profile indicative of the concentration of analyte particles.

The analyte substance may be a fluid, gel or other material containing analyte particles and allowing diffusion of analyte particles into and out of the substance. A diffusion substance may similarly be a fluid, gel or other material containing binding particles and allowing diffusion of analyte particles into and out of said substance. As discussed above, only one of these substances needs to be capable of allowing diffusion. The other can be a solid. The dynamic viscosities of the analyte and diffusion substances are, independently, preferably between about one and about four times the dynamic viscosity of water, e.g., between about 0.01 and about 0.04 poise. These substances may be placed in side-by-side contact in or on any suitable container, e.g., on a plane surface, a sample well, tube or space formed between adjacent layers of material, allowing interrogation by a detection instrument such as a CCD camera. In a preferred embodiment, binding particles are dispersed in a gel that retains its shape and which contains a solvent capable of allowing analyte particles to diffuse therein. A drop-sized hollow is formed in the gel and a drop of analyte fluid, e.g., blood, is dropped into the hollow. The diffusion profile of labeled analyte particles is detected in the area of the gel surrounding the drop.

This invention also provides a microscale device for determining the presence or concentration of sample analyte particles in an analyte fluid comprising: a laminar flow channel comprising an analyte stream inlet and a diffusion stream inlet; said laminar flow channel comprising, in adjacent laminar flow: an analyte stream containing said analyte fluid to which additional analyte particles labeled with a detectable marker have been added to provide a predetermined concentration of labeled analyte particles in said analyte fluid; and a diffusion stream containing binding particles capable of binding to said sample analyte particles and said labeled analyte particles; said device further comprising means for detecting a diffusion profile in said channel formed by said labeled analyte particles; and means for determining from said diffusion profile the presence or concentration of said sample analyte particles.

As discussed above, any detection means known to the art may be used for detecting the diffusion profile. CCD cameras or laser scanners with photomultipliers are preferred detection means. In the latter, a laser is scanned back and forth across the channel by means of a piezoelectric drive. A photo multiplier tube is placed to detect the position of the laser spot and coupled to software to calculate the diffusion profile from the laser signal and position.

Also as discussed above, preferred means for determining the presence or concentration of analyte particles include a computer processor programmed to calculate said presence or concentration of analyte particles based on an algorithm utilizing process variables. Such variables include those selected from the group consisting of flow rates of said fluids, diffusion coefficients of said binding particles, said analyte particles, labeled analyte particles, and labeled analyte/binding particle complexes, concentrations of said binding particles and labeled analyte particles, diffusion dimension of the device, channel length from channel inlets to detection zone, and binding kinetics of the analyte and binding particles.

The devices of this invention may also comprise a reference stream inlet to allow a reference or control stream to flow in laminar flow contact with the diffusion and analyte streams in the laminar flow channel. Such devices therefore include a reference stream inlet into said laminar flow channel constructed and arranged such that said reference stream can flow in laminar flow contact with said diffusion stream, and a reference stream comprising a known concentration of labeled analyte particles and a known concentration of unlabeled analyte particles.

BRIEF DESCRIPTION OF THE FIGURES

FIG. 1A shows initial conditions in an interdiffusion competition assay. Two volumes of fluid are placed into interdiffusive contact. One fluid contains a high molecular weight binding molecule such as specific antibody (Ab) (left side). The other fluid (right side) contains at least labeled (label shown by square-shaped particles) conjugate of the antigen to be monitored (LA) and sample antigen (SA) (irregular particles). FIG. 1B is a schematic representation of the concentration of LA across the diffusion dimension at an early stage of diffusion (free (LA), antibody-bound (AbLA), and total (LA+AbLA)). Here, the initial concentrations of Ab are much greater than LA+SA, allowing a significant fraction of LA and SA to bind. FIG. 1C is a schematic representation of the case when Ab is much less than LA+SA. A small fraction of antigen molecules are able to bind due to the saturation of binding sites resulting in a diffusion profile more similar to that of free diffusion. Less LA accumulates near the fluid interface.

FIG. 2 depicts the T-sensor apparatus for conducting the diffusion immunoassay in a T-Sensor.

FIG. 3A shows diffusion profiles of phenytoin LA imaged across the d-dimension at one location downstream from the inlet junction, showing diffusion profiles at four different rates of pumping of both solutions through the channel. FIG. 3B shows data from pumping different concentrations of Ab specific to phenytoin through the left side of the channel. A fixed concentration of LA was pumped through the right side of the channel (no SA was present).

FIG. 4A is a plot of intensity profiles measured across the d-dimension of the T-Sensor for sample antigen (SA) from 50 nM to 1.6 $\mu$M. FIG. 4B plots the first derivative of the intensity profiles with respect to distance across the d-dimension. FIG. 4C plots the maximum (circles) and minimum (squares) slope values in the regions of interest vs. the concentration of SA tested, the maximum values being taken from the drop-off region and the minimum values being taken from the accumulation region, for use as calibration curves.

FIG. 5A shows diffusion profiles generated with the analytical model useful for general DIA design. The variable C is a non-dimensionalized parameter that can be used to set values for the five related parameters to generate the set of diffusion profiles plotted. The five parameters are time, SA, LA, and Ab concentrations, and d. FIG. 5B shows the results of the phenytoin DIA as predicted by the analytical model based on the experimental conditions.

DETAILED DESCRIPTION OF THE INVENTION

Microfluidics is rapidly becoming a cornerstone technology in chemical diagnostics and the microfluidic diffusion immunoassay (DIA) of this invention is a useful tool for many diagnostic applications. In microfluidic channels, fluids usually show laminar behavior. This allows the movement of different fluidic layers next to each other in a channel without mixing other than by diffusion. For example, in the device and methods of U.S. Pat. No. 5,948,684, a sample solution (e.g., whole blood), and a receptor solution (e.g., an indicator solution), and optionally, a reference solution (a known analyte standard) are introduced in a common channel (T-Sensor™), and flow next to each other until they exit the structure. Smaller particles such as ions or small proteins diffuse rapidly across the fluid boundaries, whereas larger molecules diffuse more slowly. Large particles (e.g., blood cells) show no significant diffusion within the time the two flow streams are in contact. Two interface zones are formed between the fluid layers. The ratio of a property (e.g., fluorescence intensity) of the two interface zones is a function of the concentration of the analyte, and is largely free of cross-sensitivities to other sample components and instrument parameters.

By taking advantage of differences in the diffusion coefficients of small molecules bound and unbound to much larger molecules, this invention provides an immunoassay format offering many advantages over conventional formats. This diffusion immunoassay (DIA) is well suited to implementation using microfluidic technology, which offers the advantages of small reagent and sample volumes, continuous monitoring capabilities, low-cost mass production of devices, and integrated testing networks amenable to automation.

DIAs can be designed to work in T-Sensors, however, they do not require a T-Sensor to function. They can also function in the H-diffusion format described, for example in U.S. Pat. No. 5,932,100 and U.S. application Ser. No. 09/346,852, or in devices providing only a single flow channel, including an open channel without a cover such as a cover slip, in channels on a porous plate, or channels formed two plates without channel walls.

Figure 1:
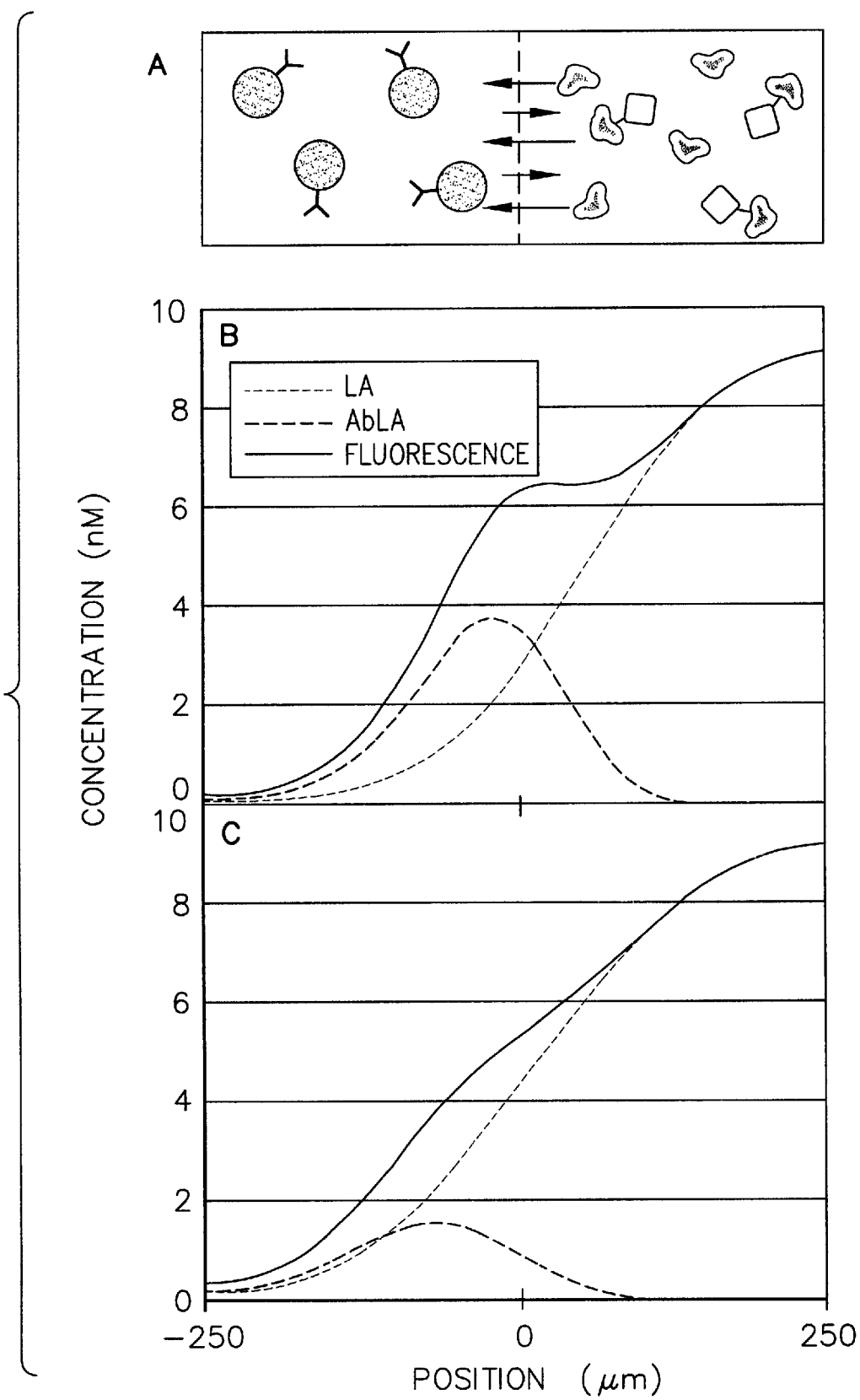
FIG. 1 is a schematic presentation of the diffusion immunoassay.

In its simplest form, the DIA uses a fluid containing sample antigen (SA) (also referred to herein as "analyte fluid" spiked with a known (predetermined) amount of labeled antigen (LA) (also referred to herein as "labeled analyte") placed in contact with a fluid containing a known concentration of antibody (Ab) (FIG. 1A) (also referred to herein as "diffusion fluid"). Two volumes of these fluids are placed into interdiffusive contact. The diffusion fluid contains a high molecular weight binding particle such as specific antibody (Ab). The analyte fluid contains at least labeled conjugate of the antigen to be monitored (LA) and sample antigen (SA). It may also contain diffusing and non-diffusing interferent compounds. FIG. 1B is a schematic representation of the concentration shown by detection of fluorescence of LA across the diffusion dimension at an early stage of diffusion for (free (LA), antibody-bound (AbLA), and total fluorescence (LA+AbLA)). LA and SA are much smaller and diffuse more rapidly than Ab. Here, the initial concentrations of Ab are much greater than LA+SA, allowing a significant fraction of LA and SA to bind. Bound antigen molecules diffuse much slower, resulting in an accumulation of signal near the fluid interface. FIG. 1C is a schematic representation of the case when Ab is much less than LA+SA. A small fraction of antigen molecules are able to bind due to the saturation of binding sites resulting in a diffusion profile more similar to that of free diffusion. Less LA accumulates near the fluid interface.

Over a given time interval, SA and LA "interdiffuse" with the Ab solution. Small antigen molecules (MW 10 kD) will diffuse about 10-fold faster than large Ab molecules (MW~150 kD). As LA and SA diffuse into the Ab solution, binding to Ab (creating either AbSA or AbLA) will significantly slow their diffusion. Thus the number of Ab binding sites relative to the concentration of total antigen will determine the distribution, or "diffusion profile," of antigen. Although the concentrations of LA and SA may be significantly different, the same fractions of LA and SA will be bound to Ab (assuming that the two species have similar diffusion and binding coefficients). Consequently, the diffusion profile of LA, the observed profile, is representative of the profile of total antigen. If the amount of Ab is much greater than the total labeled and unlabeled antigen, diffusion of LA will be maximally affected by binding events as shown in FIG. 1B resulting in an accumulation of LA shortly after diffusing into the Ab solution. If the amount of Ab is much less than the labeled and unlabeled antigen, the diffusion profile of LA will be less affected by binding events, as shown in FIG. 1C.

The diffusion profile is most sensitive to changes in antigen concentration when (SA concentration+LA concentration)=Ab concentration, and when LA concentration and Ab concentration are fixed, SA concentration determines the diffusion profile of LA.

Figure 2A:
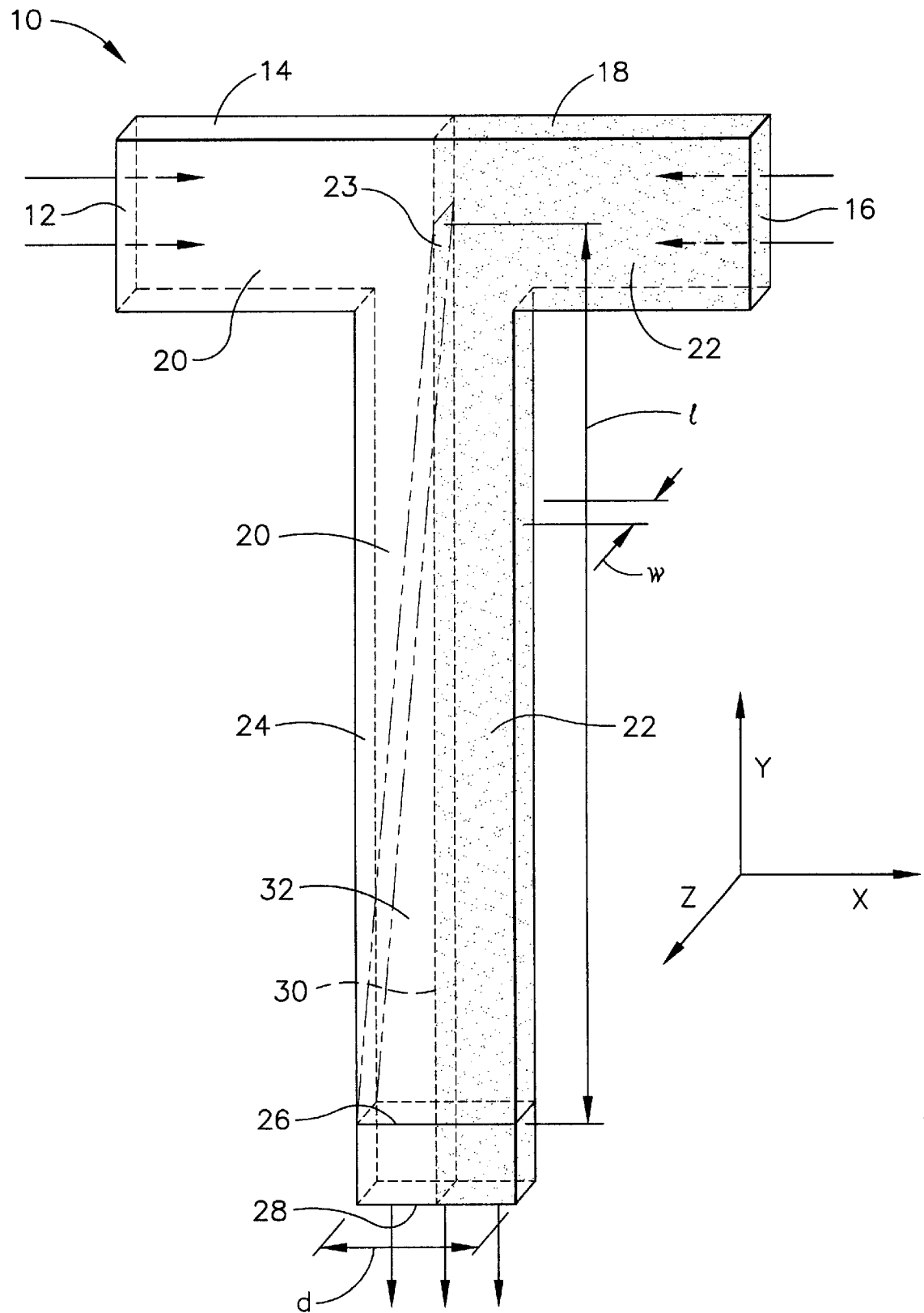
FIG. 2A is a schematic showing diffusion of antibody (AB) (left side), and labeled antigen (LA) (right side).

Laminar flow conditions and diffusion-dependent mixing achieved with a two-inlet T-Sensor were used to test the DIA concept. The T-sensor concept is illustrated in FIG. 2A. At low Reynolds number conditions, preferably less than 1, the flows of the sample antigen (pre-mixed with labeled antigen) and the antibody solution run parallel to each other and do not mix except by diffusion. The concentration of a label such as a fluorophore can be monitored at any point downstream from the entry ports using a one-or two-dimensional detector array. If the device is relatively thin (in the w dimension), all components rapidly equilibrate along that axis and the problem can be treated using a one-dimensional analysis. If more than two streams are introduced into the device, it can be configured to include a reference or control material to provide a simultaneous one-point calibration of the device (J. W. Paxton, F. J. Rowell, J. G. Ratcliffe, *J. Immunol. Methods* 10, 317–27 (1976)).

FIG. 2A shows T-sensor 10 having diffusion stream inlet 12 leading into diffusion stream channel 14, and analyte stream 16 leading into analyte stream channel 18. These channels, 14 and 18, meet to form laminar flow channel 24, which ends in laminar flow channel outlet 28. Diffusion stream 20 and analyte stream 22 meet at inlet junction region 23 and flow together in laminar flow in laminar flow channel 24.

Two solutions, one containing Ab and referred to herein as diffusion stream 20, and the other containing both LA and SA, and referred to herein as analyte stream 22, are pumped into inlets 12 and 16 at equal, constant flow rates. Under low Reynolds number conditions, the flow streams run parallel to each other in the laminar flow channel 24 and do not mix except by diffusion. The midline 30 of laminar flow channel 24 is shown by a dotted line. Interdiffusion zone 32 on either side of midline 30 is the area in which analyte particles are diffusing into the left side of the laminar flow channel 24 and binding particles are diffusing into the right side of laminar flow channel 24.

Diffusion across the diffusion dimension (d-dimension) is dependent on time, which is controlled in the T-Sensor by flow rate and the traversed length (l) of the main channel. The diffusion profile along the d-dimension can be held at a steady state at any distance l by maintaining the flow rate, allowing continuous monitoring of the diffusion profile using one- or two-dimensional detector arrays. To infer the concentration of SA, the concentration profile of LA across the d-dimension of the main channel is measured at an appropriate distance l along laminar flow channel 24 at detection zone 26. At inlet junction region 23 of the two streams, there is a flow development region in which the flow velocity is less than that in the fully developed flow downstream. We ignore this effect in analytical modeling because it is insignificant at greater than about 1 mm downstream where measurement occurs. In this Figure, the y coordinate indicates the length dimension (l), the z coordinate indicates the diffusion dimension or depth (d), and the x coordinate indicates the width dimension (w).

Figure 2B:
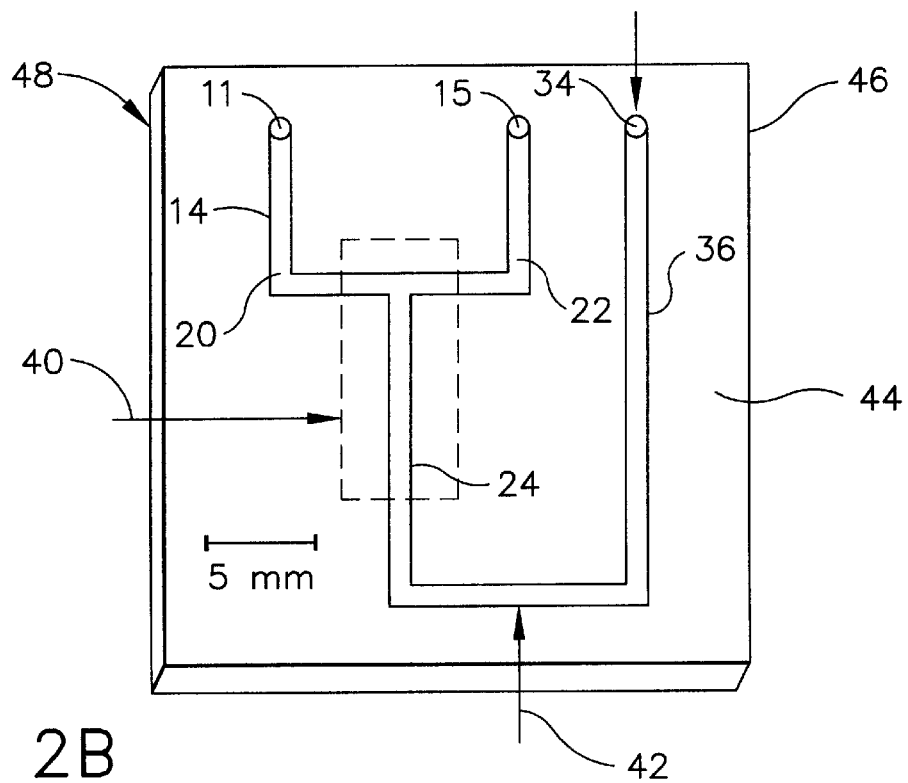
FIG. 2B shows further aspects of the device.

The T-Sensor used for testing the principles of DIA is shown in FIG. 2B, a diagram of the microfluidic device used in the Example hereof. It utilizes top glass cover slip 44 and bottom glass cover slip 46. In top glass cover slip 44, three round holes or ports, diffusion stream inlet port 11, analyte stream inlet port 15, and drain port 34, are drilled for access respectively to the diffusion stream channel 14, analyte stream channel 18, and drain channel 36. Between cover slips 44 and 46 is a piece of 100 μm thick Mylar chip 48 coated on both sides with adhesive (Fraylock, Inc., San Carlos, Calif.), through which the channels were cut using a carbon dioxide laser cutting system (Universal Laser Systems). The laminar flow channel 24 is 750 μm wide in the d-dimension (scale bar=5 mm).

Figure 2C:
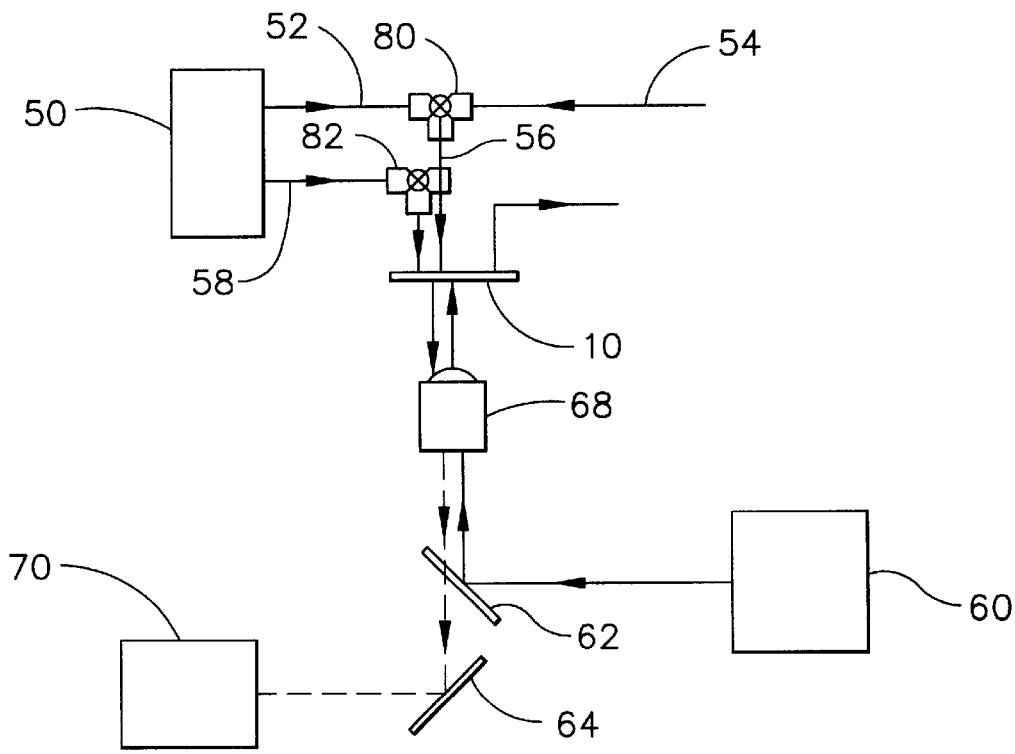
FIG. 2C is a block diagram of the apparatus employed to acquire the data presented in the Example hereof.

FIG. 2C is a block diagram of the apparatus employed to acquire the data presented in the Example hereof. Reagents were manually loaded into the fluid lines (polyetheretherketone tubing, Upchurch Scientific) and then pushed through the device using a Kloehn syringe pump 50. Sample analyte conduit 52 contains the sample fluid. Labeled analyte conduit 54 contains labeled analyte to be mixed with the sample fluid containing sample antigen and flows into analyte conduit 56 through analyte valve 80. Labeled analyte particles (fluorescein-labeled antigen) flowing through the laminar flow channel of the T-Sensor 10 were excited using a 50 W halogen lamp (Zeiss) 60 and the emission signal was magnified ten times by a Zeiss microscope 68 and captured using an integrating charge coupled device (CCD) camera (SBIG ST-71) 70. Light from lamp 60 of a wavelength capable of being reflected by dichroic mirror 62, passes through microscope 68 and is reflected from T-sensor 10. The reflected light, having wavelengths determined by labeled analyte particles in T-sensor 10, now passes through dichroic mirror 62 and is reflected from mirror 64 to the CCD camera 70. A 20% dilution of fluorescent phenytoin (fluorescein-labeled 5-5-diphenylhydantoin) reagent in 50 mM Tris-HCl pH 9.0 was used for LA (~50 nM based on fluorescence intensity measurements using Perkin Elmer LS50B).

Figure 6:
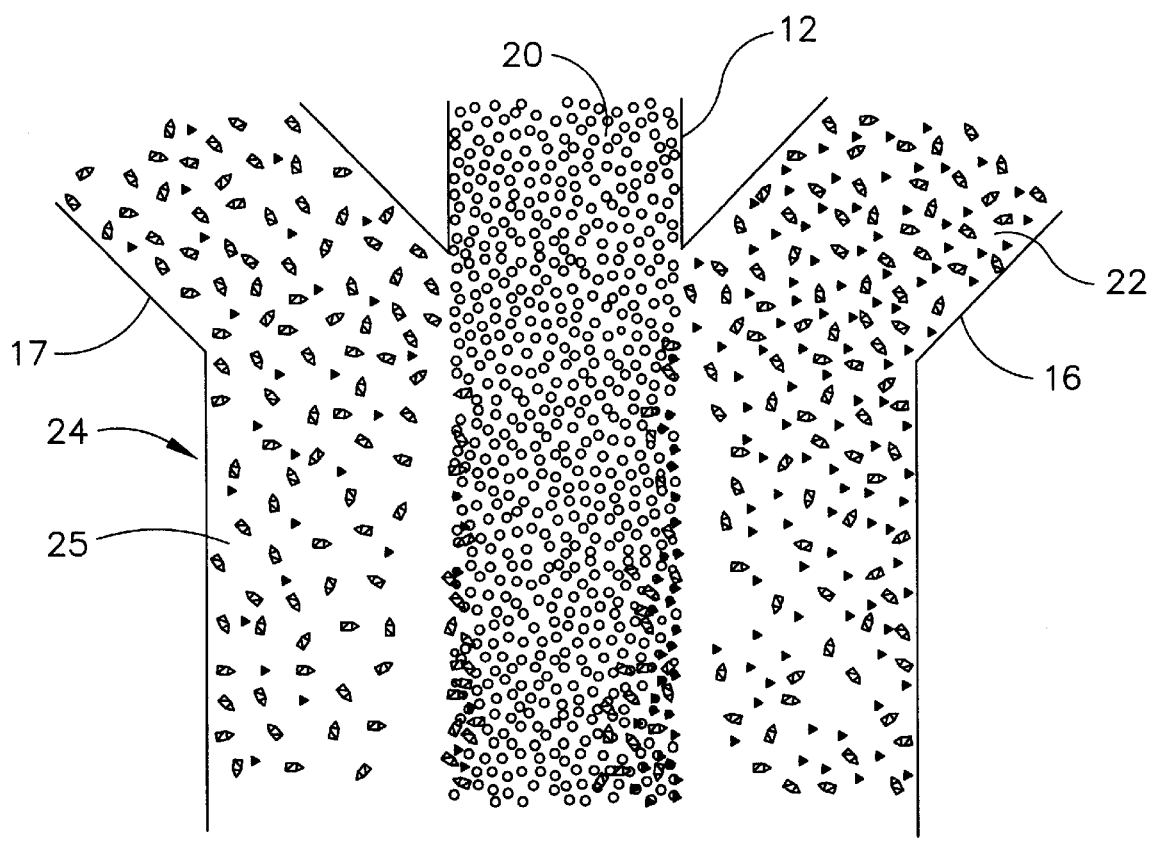
FIG. 6 shows an embodiment of this invention utilizing a reference stream in the laminar flow channel.

Another embodiment of the present invention is shown in FIG. 6, which uses a third, reference, stream in the laminar flow channel. The device requires a laminar flow channel 24, a reference stream inlet 17, a diffusion stream inlet 12, and an analyte stream inlet 16. A known concentration of labeled analyte particles made up of label particles (squares) bound to sample analyte particles (triangles), and an unknown concentration of sample analyte particles, are mixed together and enter laminar flow channel 24 as analyte stream 22; diffusion stream 20 containing binding particles (circles) capable of binding to the analyte particles enters laminar flow channel 24 through diffusion stream inlet 12. A mixture of a known concentration of labeled analyte particles and a known concentration of unlabeled analyte particles enters the laminar flow channel 24 through reference stream inlet 17 as reference stream 25; analyte particles (unbound, both labeled and unlabeled) diffuse quickly from analyte stream 22 into the center diffusion stream 20 and compete for binding particles. As soon as the analyte particles are bound, diffusion substantially slows. The higher the analyte concentration, the more labeled analyte particles will remain unbound and diffuse further into the center stream. A CCD image of a detection area within the laminar flow channel 24 shows, with increased analyte concentration, an increase of fluorescence in the center of the channel and a decrease of fluorescence in the portions of the sample and reference streams next to the center stream. The same thing happens on the reference side of laminar flow channel 24 as labeled and unlabeled analyte particles diffuse into the diffusion stream 20 from reference stream 25. The diffusion profile (pattern of fluorescence) on the reference stream side of the center stream and on the analyte side of the center stream are compared and used to determine the concentration of analyte particles in analyte stream 22.

Figure 7:
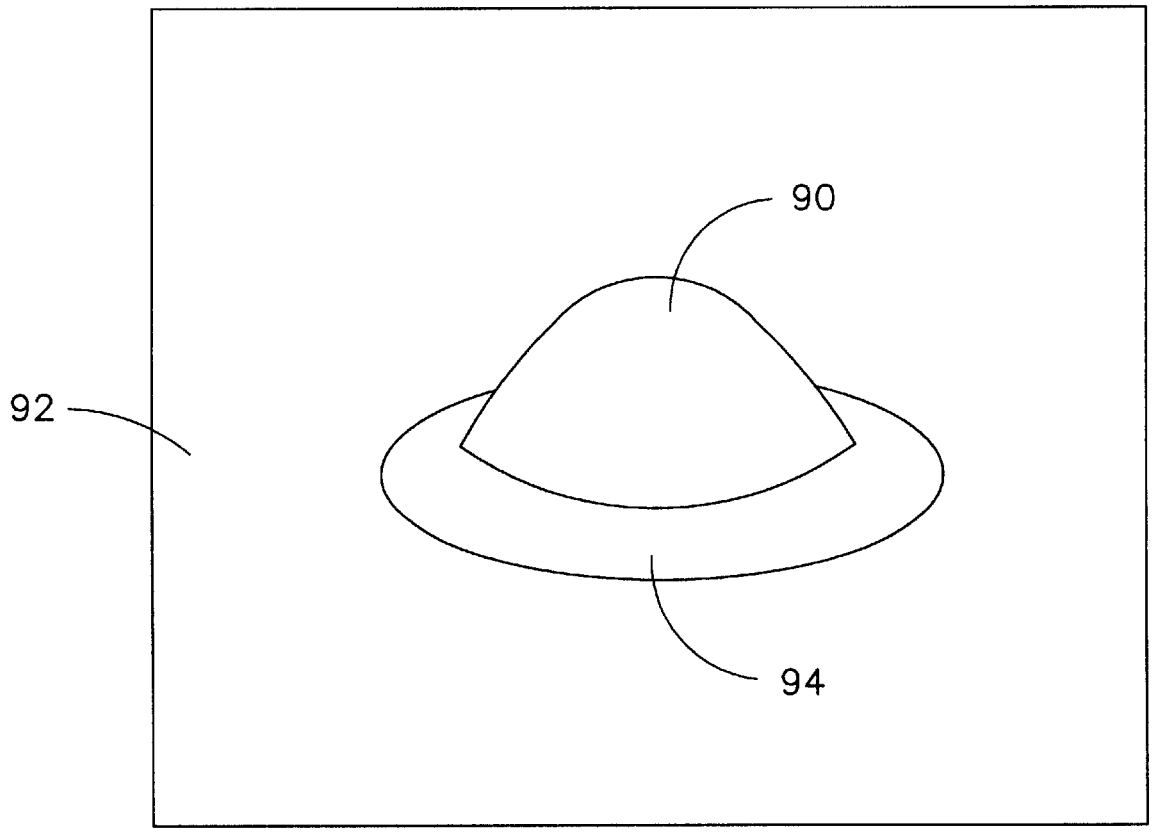
FIG. 7 shows a non-flowing embodiment of this invention

FIG. 7 shows another embodiment of this invention utilizing separate carrier substances for the binding particles and the analyte particles. Sample analyte and labeled analyte particles may be suspended in a fluid or gel analyte substance 92 placed in contact with a fluid or gel diffusion substance 90. Analyte particles and labeled analyte particles diffuse into diffusion zone 94.

For example, the sample analyte substance might be whole blood, and the diffusion substance might be a gel or viscous solution containing an antibody to a desired antigen on which a drop of whole blood was placed.

Alternatively, the analyte substance might be used in larger quantities, and a small amount of diffusion substance placed thereon.

Viscosity modifiers such as dextran, salts, sugars or others known to the art might be used to provide viscosities producing diffusion zones and diffusion profiles which are readily analyzable.

Figure 8:
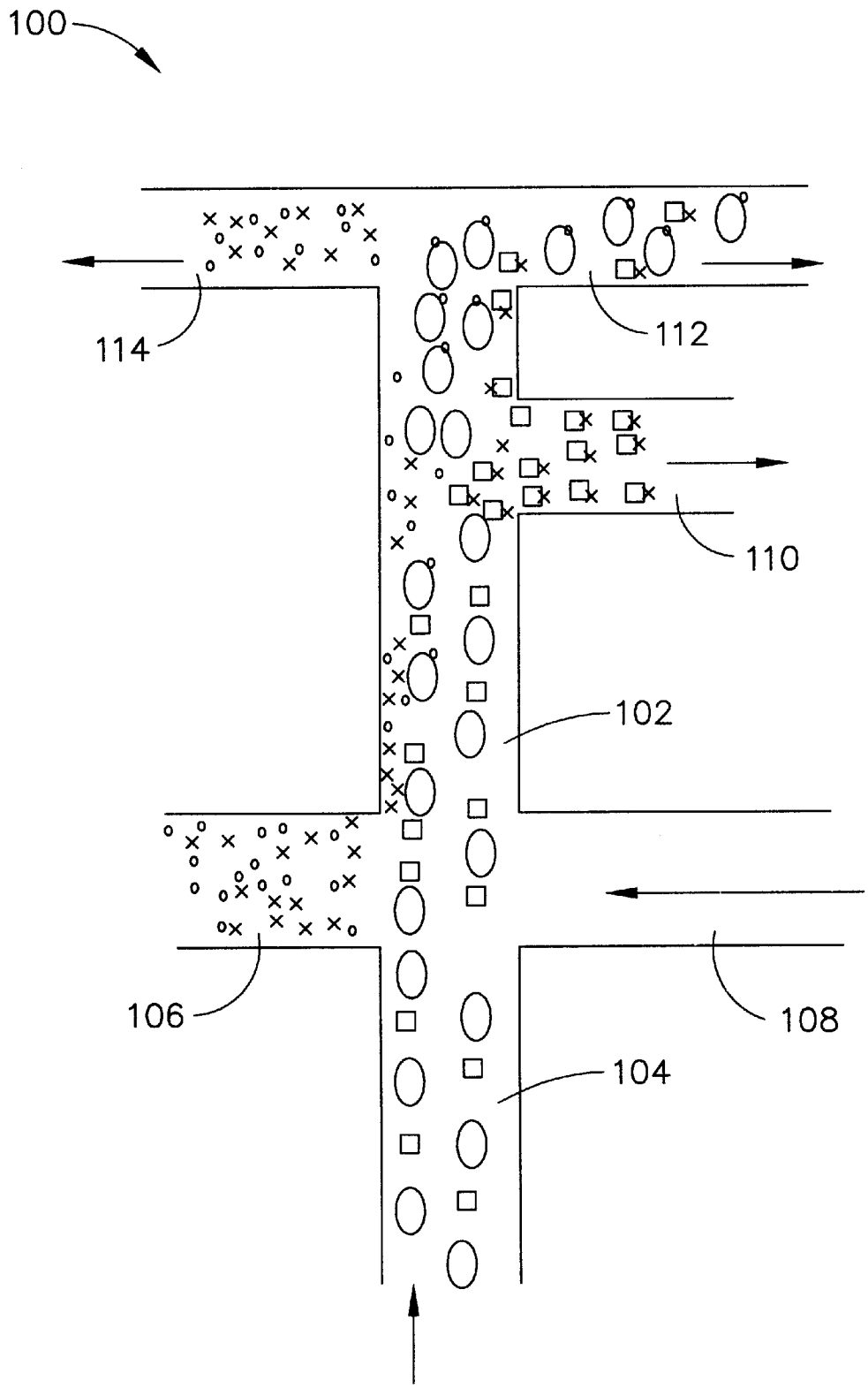
FIG. 8 shows a microfabricated diffusion separator suitable for use in practicing the separation process of this invention. □ are smaller binding particles. ○ are larger binding particles. Small x's and o's represent small particles to be separated.

FIG. 8 depicts a diffusion separator used for separating small particles of similar size. The separator 100 comprises a flow channel 102 having a mixed binding particle inlet channel 104, mixed small particle inlet channel 106 and acceptor stream inlet channel 108. Downstream from the inlets is a smaller complex outlet channel 110, and downstream from that is a mixed complex outlet channel 112 and, optionally, a small particle residue outlet channel 114.

In operation, a stream containing smaller and larger binding particles is flowed into flow channel 102 through mixed binding particle inlet channel 104. The smaller binding particles are represented by squares, and the larger binding particles are represented by larger circles. A first fluid containing mixed small particles, represented by small x's and o's, is also flowed into flow channel 102 through mixed small particle inlet channel 106. The small particles diffuse into the stream containing the binding particles, where they form complexes. The binding particles represented by the squares are capable of complexing with the small particles represented by x's, and the binding particles represented by the circles are capable of complexing with the small particles represented by the o's. After formation of complexes, the smaller complexes, represented by the squares with attached x's, diffuse more rapidly into the acceptor stream, and may be removed in a stream containing smaller complexes and little or no larger complexes. This stream, which flows from flow channel 102 through smaller complex outlet channel 110, may also contain some unbound small particles. The larger complexes, which diffuse more slowly than the smaller complexes, together with remaining smaller complexes, flow out of channel 102 through mixed complex outlet channel 112 downstream from smaller complex outlet channel 110. Residual smaller particles may exit small particle residue outlet channel 114. Additional H-filter separators may be attached to outlets 110 and 112, in series as needed to further separate particles in the exiting streams by size. Detectors may be placed anywhere in the system, e.g., in the flow channel to detect the diffusion front formed by the smaller complexes and the diffusion front formed by the larger complexes, or in any of the outlet channels.

Figure 9:
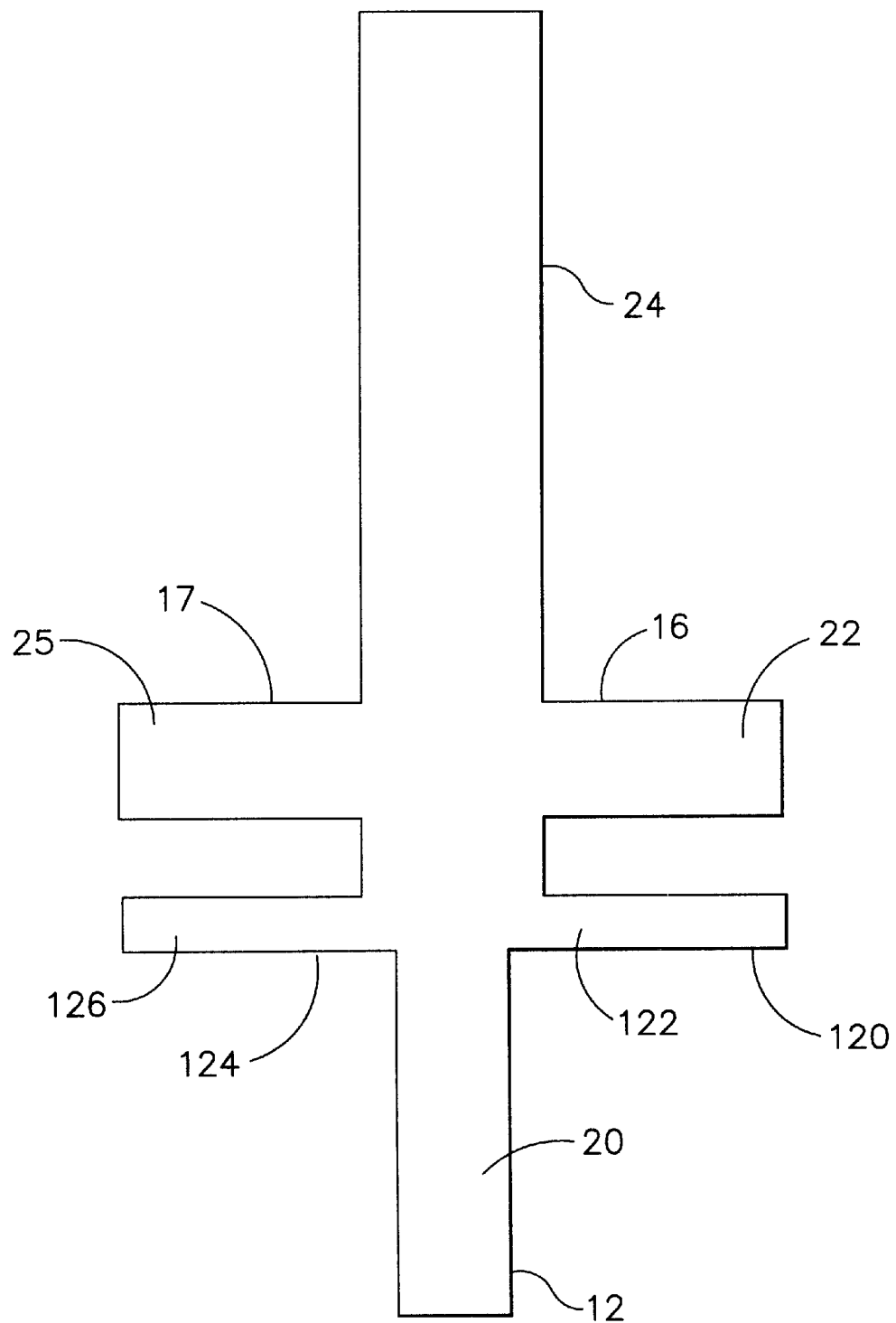
FIG. 9 is a schematic representation of an embodiment of this invention utilizing inert separation streams.

FIG. 9 is a schematic representation of an embodiment of this invention utilizing inert separation streams. Laminar flow channel 24 in fluid communication with analyte stream inlet 16 containing analyte stream 20, reference stream inlet 17 containing reference stream 25, and diffusion stream inlet 12 containing diffusion stream 20 are as described above with respect to FIG. 6. In addition, first inert separation stream inlet 120 containing first inert separation stream 122, and second inert separation stream inlet 124 containing second inert separation stream 126, in fluid communication with laminar flow channel 12 are placed upstream from analyte stream inlet 16 and reference stream inlet 17 such that first inert separation stream 122 flows in laminar flow between analyte stream 22 and diffusion stream 20, and second inert separation stream 126 flows in laminar flow between reference stream 25 and diffusion stream 20.

The separation streams are narrow enough so that they do not substantially interfere with diffusion of analyte particles into the diffusion stream 20, i.e., such that they do not prevent obtaining and analyzing test data from the system. The separation streams, however, are wide enough to prevent larger molecules in the reference, diffusion and analyte streams from contacting each other by virtue of the side-by-side flow of the streams. Preferably the separation streams 122 and 126 are between about 2 $\mu$m and about 20 $\mu$m.

In systems where the analyte and/or reference stream may contain large particles which are reactive with indicators such as antibodies or other particles such as dyes in the diffusion stream, it is desirable to prevent direct contact of the streams. For example, in systems such as the phenytoin assay, fluorescent particles may be sensitive to albumin or other proteins in the analyte stream. To prevent interference by such proteins, a separation stream is effective because these larger molecules do not substantially diffuse across the separation stream to contact and react with indicators in the diffusion stream.

Any fluid which does not contain particles which react with analyte particles or indicators in the system may be used to form the inert separation streams, e.g., water or buffer. The inert separation streams may be miscible or immiscible with the other streams. Inert separation streams may be used to separate adjacent laminar flow streams in all embodiments described herein.

EXAMPLE

The diffusion immunoassay of this invention was used to determine the concentration of phenytoin (diphenylhydantoin), an anti epileptic drug in a liquid sample. It is necessary to monitor individual responses to treatment with this drug in a narrow therapeutic range (J. W. Paxton, F. J. Rowell, J. G. Ratcliffe, *J. Immunol. Methods* 10, 317–27 (1976); A. R. McGregor, J. O. Crookall-Greening, J. Landon, D. S. Smith, *Clin. Chim. Acta* 83, 161–6 (1978)). Many testing formats, both homogeneous and heterogeneous, have been developed for therapeutic monitoring of phenytoin concentrations, including the fluorescence polarization immunoassay (FPIA) (A. R. McGregor, J. O. Crookall-Greening, J. Landon, D. S. Smith, *Clin. Chim. Acta* 83, 161–6 (1978)), a spin immunoassay (M. R. Montgomery, J. L. Holtzman, R. K. Leute, J. S. Dewees, G. Bolz, *Clin. Chem.* 21, 221–6 (1975)), a radio-immunoassay (J. W. Paxton, F. J. Rowell, J. G. Ratcliffe, *J. Immunol. Methods* 10, 317–27 (1976)), and an enzyme immunoassay (H. E. Booker and B. A. Darcey, *Clin Chem* 21, 1766–8 (1975)).

To develop a microfluidic immunoassay, we chose to adapt the contents of a proprietary FPIA kit used for automated measurement of phenytoin concentration (Sigma Chemical Co., St. Louis, Mo.). Fluorescently labeled phenytoin and specific antibody from the kit were used as stock solutions for LA and Ab respectively. A feature of the assay of the present invention using a reference stream is that uncharacterized reagents can be used in a quantitative assay, as long as a calibration curve can be generated. A cooled CCD camera was used to capture images of the fluorescence intensity profile of LA across the d-dimension of the flow cell shown in FIG. 2C.

Figure 3:
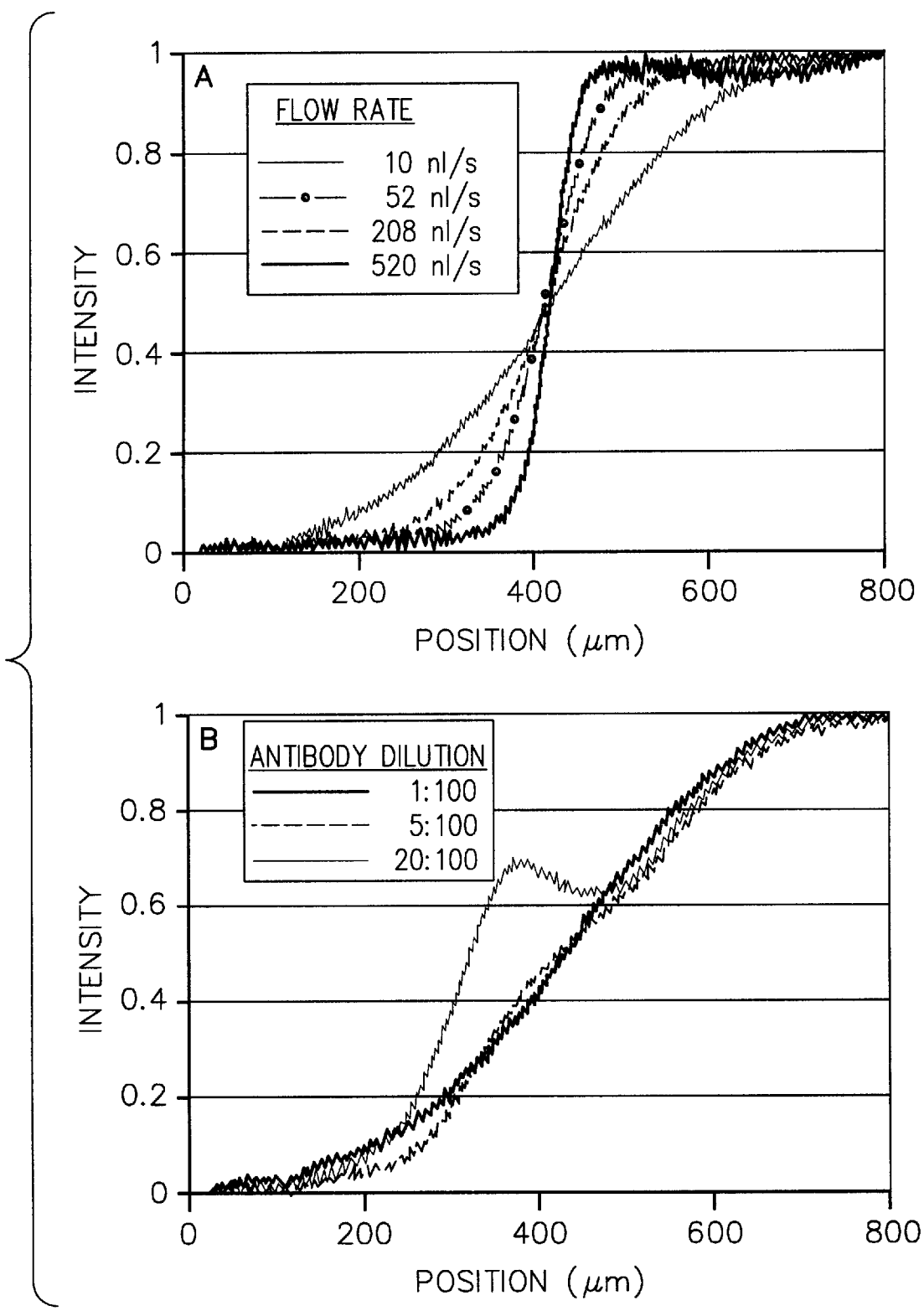
FIG. 3 shows data used for determination of suitable test parameters for the phenytoin DIA described in the Example hereof.
Figure 4:
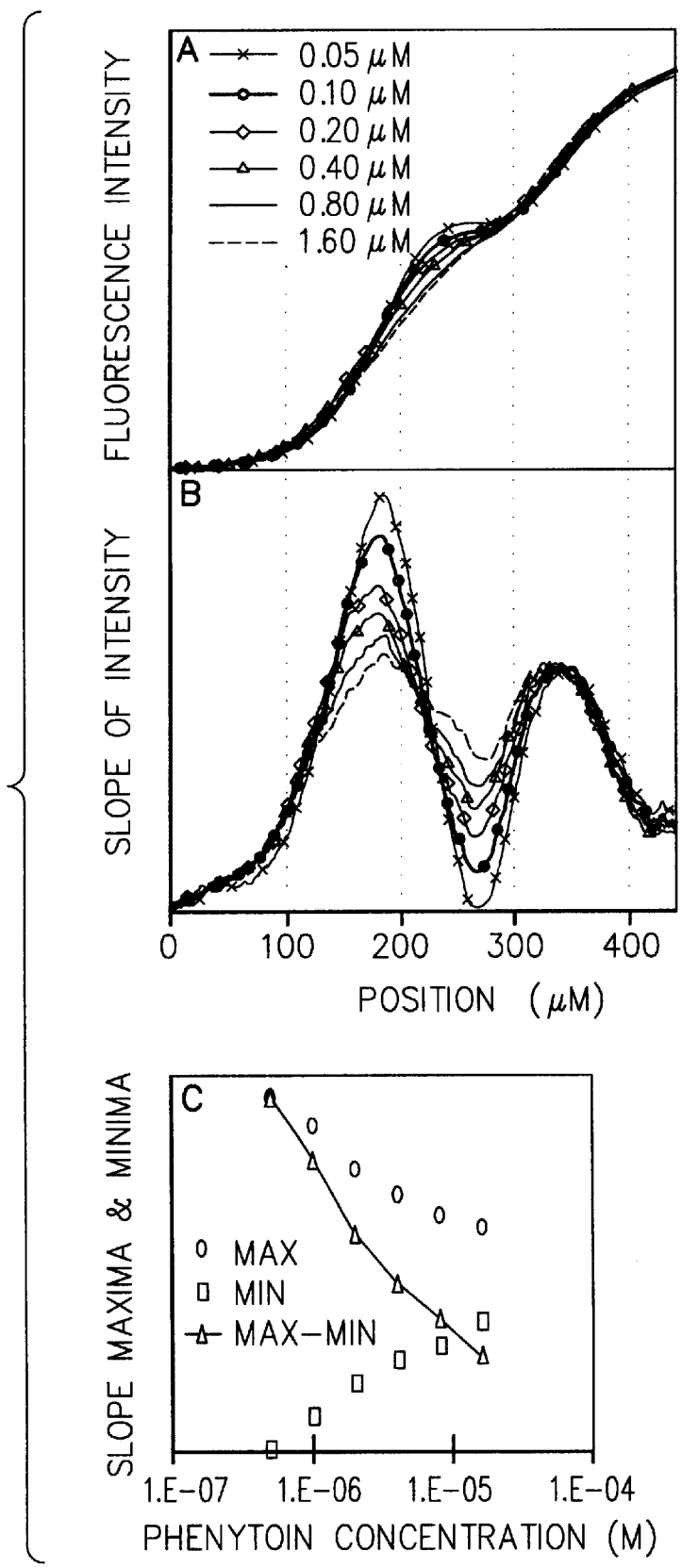
FIG. 4 shows experimental results of the phenytoin DIA.

To experimentally determine the time required for appreciable diffusion of LA across the d-dimension in the absence of Ab, diffusion profiles of LA were measured at a fixed distance l at different flow rates (FIG. 3A). Diffusion profiles of phenytoin LA were imaged across the d-dimension at one location downstream from the inlet junction, showing diffusion profiles at four different rates of pumping of both solutions through the channel. Buffer was pumped through the left side of the device, and LA was pumped through the right side. Note that at slower pumping rates the diffusion of the LA has proceeded further into the left side of the device. These data were used to determine an effective flow rate and distance l for DIA measurements of phenytoin. Based on these data, a flow rate of 52 nl/s through the main channel was used for DIA experiments, and measurements of the diffusion profile were taken at l=10 mm. This corresponds to an average interdiffusion time of 14.4 seconds based on the time required for the bulk fluid to traverse the distance l at this flow rate (neglecting the short residence time in the developing flow region at the inlet junction).

To determine a concentration of Ab effective in altering the diffusion of LA with SA=0, the interdiffusion of LA with different concentrations of Ab was measured as shown in FIG. 3B. Different concentrations of Ab specific to phenytoin were pumped through the left side of the channel. A fixed concentration of LA was pumped through the right side of the channel (no SA was present). When a sufficient concentration of Ab was present, a large fraction of LA molecules were able to bind to Ab, and LA accumulated near the fluid interface, as predicted. When low concentrations of Ab were present, a small fraction of LA bound to Ab, and the majority of LA diffused freely. This method can be used to determine the appropriate concentration of Ab to employ in the assay, even if that solution is otherwise uncharacterized. The diffusion profile of LA was significantly affected when a 20% dilution of phenytoin antibody reagent in 50 nM Tris HCl pH 9.0 was used. This concentration of Ab was used for subsequent DIA measurements.

Experimental results of the phenytoin DIA for different concentrations of SA were consistent with theory, as shown in FIG. 4A which plots intensity profiles measured across the d-dimension of the T-Sensor for SA concentrations from 50 nM to 1.6 $\mu$M. As predicted, when lower SA concentration was present, a larger fraction of LA bound to available Ab binding sites. The slowed diffusion of LA upon binding resulted in an accumulation of LA near the center of the channel. As SA concentration was increased, a smaller fraction of LA bound to available Ab binding sites, and the intensity profile of LA approached that observed for free diffusion when no Ab was present (FIG. 3A) because the Ab binding sites were saturated Different diffusion profiles were thus observed for each SA concentration tested over the range of 50 nM to 1.6 $\mu$M.

To interpret the data, the first derivative of the intensity profiles with respect to distance across the d-dimension were calculated (FIG. 4B). This generates data from which a numerical value of the effect SA has on the profile can be extracted. As the concentration of SA is reduced, the slope in the accumulation region is reduced and the slope in the drop-off region is increased. A clear trend in the slope values was observed for different concentrations of SA. Near the center of the channel, the slope values decreased as SA concentration decreased. This is due to the accumulation of LA in this region, flattening the slope that would otherwise be observed for free diffusion. On the left side of the interdiffusion zone, the slope increased as SA concentration decreased. This is due to a more drastic drop in LA concentration beyond the accumulation region. The regions of focus are therefore the slopes in the accumulation and drop-off region of the diffusion interaction zone.

A plot of the minimum slope values from the accumulation region and maximum slope values from the drop-off region of the intensity profiles provides a suitable calibration curve for measuring SA concentration as shown in FIG. 4C which plots the maximum (circles) and minimum (squares) slope values in the regions of interest vs. the concentration of SA tested. The maximum values were taken from the drop-off region and the minimum values were taken from the accumulation region. Either of these trends can serve as a calibration curve, but the difference of these two trends (triangles) provides better sensitivity.

The DIA can be described by a set of five partial differential equations.

$$\frac{\partial[LA]}{\partial t} = D_{LA}\left(\frac{\partial^2[LA]}{\partial x^2}\right) - k_1\left([LA][Ab] - \frac{[AbLA]}{K_{eq}^1}\right) \quad (1)$$

$$\frac{\partial[SA]}{\partial t} = D_{SA}\left(\frac{\partial^2[SA]}{\partial x^2}\right) - k_2\left([SA][Ab] - \frac{[AbSA]}{K_{eq}^2}\right) \quad (2)$$

$$\frac{\partial[Ab]}{\partial t} = D_{Ab}\left(\frac{\partial^2[Ab]}{\partial x^2}\right) - k_1\left([LA][Ab] - \frac{[AbLA]}{K_{eq}^1}\right) - k_2\left([SA][Ab] - \frac{[AbSA]}{K_{eq}^2}\right) \quad (3)$$

$$\frac{\partial[AbLA]}{\partial t} = D_{AbLA}\left(\frac{\partial^2[AbLA]}{\partial x^2}\right) + k_1\left([LA][Ab] - \frac{[AbLA]}{K_{eq}^1}\right) \quad (4)$$

$$\frac{\partial[AbSA]}{\partial t} = D_{AbSA}\left(\frac{\partial^2[AbSA]}{\partial x^2}\right) + k_2\left([SA][Ab] - \frac{[AbSA]}{K_{eq}^2}\right) \quad (5)$$

where $D_N$ is the diffusion coefficient for species N, $k_1$ and $k_2$ are the forward reaction rate constants for the LA-Ab reaction and the SA-Ab reaction respectively, and $K_{eq}{}^1$ and $K_{eq}{}^2$ are the equilibrium constants for the same two reactions. Coordinate axes are those used in FIG. 2A. Note that [Ab] is the concentration of individual Ab binding sites, and is therefore equal to twice the concentration of Ab molecules. A more detailed use of the analytical model applied to similar T-Sensor work has been published elsewhere (A. E. Kamholz, B. H. Weigi, B. A. Finlayson, P. Yager (1999), *Anal. Chem.*, 71(23):5340–5347.

To determine the detection range for any particular DIA, a numerical model can be employed to solve this system of equations for a given set of starting concentrations and diffusion time. As typical antigen and antibody molecular weights are 1 kD and 150 kD, respectively, values for diffusion coefficients, D, of DLA=DSA=$3.19\times10^{-6}$ $cm^2/s$ and DAB=$4.30\times10^{31\ 7}$ $cm^2/s$ were used (C. Bor Fuh, S. Levin, J. C. Giddings, *Anal. Biochem.* 208, 80–7 [1993]). Also, since both antigens are small compared to the antibody, it was assumed that DAbLA=DAbSA=DAb. To predict the lowest detectable concentrations, an upper limit for the equilibrium constant of $1\times10^{12}$ $M^{-1}$ was used for both the LA and SA binding events (R. Ekins, *Nuclear Medicine and Biology* 21, 495–521 [1994]). A typical forward reaction rate constant of $1\times10^6$ $M^{-1}s^{-1}$ was used for both reactions (A. D. Griffiths, et al., *Embo J.* 12, 725–34 [1993]).

The analytical model is useful for evaluating the effectiveness of any given DIA strategy to determine unknown values, such as SA concentration. A set of non-dimensionalized finite-difference solutions was created using the model and stated parameters. The predicted DIA diffusion profiles were plotted (FIG. 5A). The variable C is a non-dimensionalized parameter that can be used to set values for the five related parameters to generate the set of diffusion profiles plotted. The five parameters are time, SA, LA, Ab, concentrations and d. These diffusion profiles are based on estimated diffusion coefficients for Ab of molecular weight 150 kD and small analytes of molecular weight 1 kD. To generate the set of profiles shown for detecting SA over the range of 10 nM to 2.43 $\mu$M, a value of C=1 should be used. The length of the d-dimension would then be 500 $\mu$m, Ab concentration would be 100 nM, LA concentration would be 10 nM, and the time allowed for interdiffusion would be 30 seconds. If a lower detection range was desired, more diffusion time would be necessary, the d length would be longer, and the concentrations of Ab and LA would be reduced. If different device dimensions, diffusion coefficients, concentrations, binding kinetics, or assay times were desired, the analytical model enables making of such changes.

Figure 5:
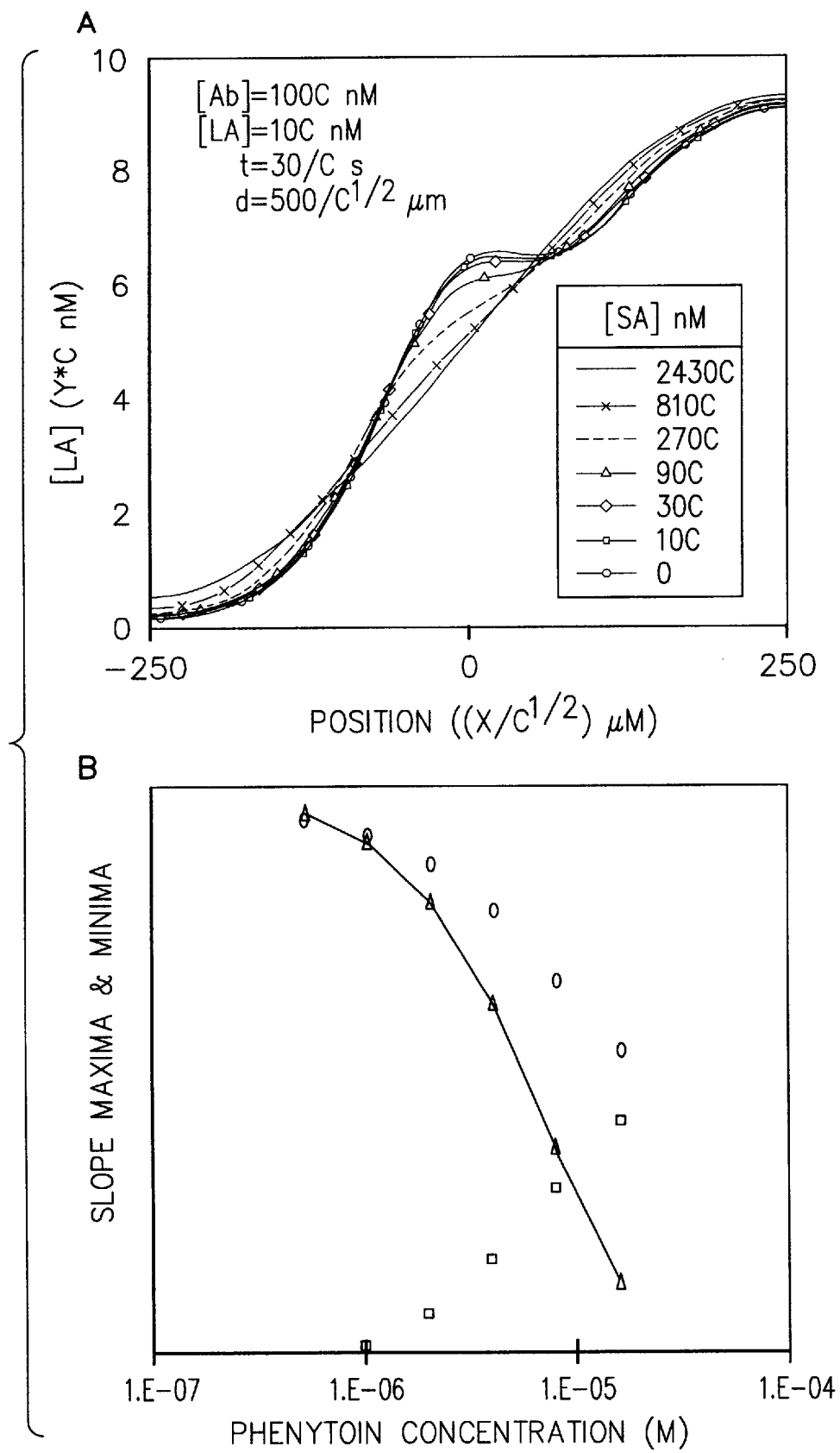
FIG. 5 shows the predictive value of an analytical model for DIA development.

FIG. 5B shows a simulation of the phenytoin DIA as predicted by the analytical model based on the experimental conditions. The result is a direct relationship between five parameters: measurement time (t), initial LA concentration, initial Ab concentration, range of SA concentrations, and size of the chamber in the d-dimension. The range of the seven SA concentrations plotted in FIG. 5A was chosen to illustrate the dynamic range of the assay for a given set of the related parameters. Dynamic range limits are apparent from the relative similarity of the profiles for the lowest two SA concentrations and the highest two concentrations. The diffusion profiles and first derivative of the diffusion profile were very similar to experimental results, showing that the model can be used to predict appropriate experimental conditions for conducting an assay. The parameters necessary for generating the model include diffusion coefficients, concentrations of Ab, SA, and LA, diffusion dimension length, channel length, and binding kinetics. In addition, values of dependent parameters can be determined by fitting experimental data to the analytical model. The binding assay method of the present invention is a useful tool for studying the properties of molecular binding reactions. For example, the binding kinetics of an altered form of a protein can be studied by comparing the characteristic DIA diffusion profiles of the native and variant form of the protein.

The DIA, a homogeneous assay, offers many advantages over conventional immunoassay formats while also extending the scope of possible measurements. By their nature, heterogeneous assays pose an immediate disadvantage; requiring the separation of immunoreagents following binding interactions. Homogeneous assays are often difficult to implement, usually requiring a change in the signal intensity of the indicator molecules due to binding events. For example, fluorescence polarization immunoassays rely on changes in the emission level of polarized light (J. M. Hicks, *Human Pathology* 15, 112–6 [1984]); and enzyme immunoassays require a change in enzyme activity caused by binding events (T. Porstmann and S. T. Kiessig, *J. Immunol. Methods* 150, 5–21 (1992)). The signal molecules used for these assays are therefore limited by their functional requirements. DIAs require only a measurement of the distribution of signal molecules across the d-dimension, and a change in the intensity of signal molecules upon binding is not required. Most conventional labeling techniques are therefore useful for DIA measurement, including absorbing, fluorescent, phosphorescent, chemiluminescent, and enzyme labels. The non-dimensionalized numerical analysis presented here shows that much lower antigen concentrations are measurable by the DIA than other assays. Practical limitations include detector sensitivity, device size, and interdiffusion time. Non-flowing implementations of DIA may also be used to increase sensitivity.

Microfluidic advantages in addition to small sample volumes and mass production of test cells are also advantages of the DIA. It has been shown that the T-Sensor can separate larger interfering components of complex samples such as blood from the reaction zone (B. H. Weigl, et al., Simultaneous self-referencing analyte determination in complex sample solutions using microfabricated flow structures (T-Sensors), μTAS '98, Banff, Canada [1998]; U.S. Pat. No. 5,948,684.) This eliminates many of the sample preparation steps that are often necessary before conducting an immunoassay. Such an advanced T-Sensor offers real-time calibration of the DIA by allowing simultaneous comparison of the sample test with the test of a known sample by adding an additional flow stream to the main channel (J. P. Brody and P. Yager, *Sensors and Actuators A (Physical)* A58(1), 13–18 (1997). The simple design is amenable to automation and can be integrated with other microfluidic testing platforms to form multi-analyte diagnostic units, the methods work directly using whole blood, the method provides higher signal intensity for a given pathlength compared to FPIA, no polarized light is required, and most standard FPIA reagent systems are useful in these systems (there are at least 20 diagnostic kits available).

As will be appreciated by those skilled in the art, numerous substitutions may be made for the components and steps disclosed herein, and the invention is not limited to the specific embodiments discussed but is to be interpreted by the broad scope of the claims appended hereto.

What is claimed is:

1. A microscale device for determining the presence or concentration of sample analyte particles in an analyte fluid comprising:
   a) a laminar flow channel comprising an analyte stream inlet and a diffusion stream inlet;
   b) said laminar flow channel comprising, in adjacent laminar flow:
      i) an analyte stream containing said analyte fluid to which additional analyte particles labeled with a detectable marker have been added to provide a predetermined concentration of labeled analyte particles in said analyte fluid;
      ii) a diffusion stream containing binding particles for binding to said analyte particles and said labeled analyte particles;
   c) means for detecting a diffusion profile in said channel formed by said labeled analyte particles;
   d) means for determining from said diffusion profile the presence or concentration of said sample analyte particles.

2. The device of claim 1 wherein said means for detecting said diffusion profile comprises a charge coupled device (CCD) camera or scanning laser.

3. The device of claim 1 wherein said means for determining comprise a computer processor programmed to calculate said presence or concentration based on an algorithm utilizing process variables.

4. The device of claim 3 wherein said process variables are selected from the group consisting of flow rates of said fluids, volumes, diffusion coefficients of said binding particles, said sample analyte particles and labeled analyte particles and labeled analyte particle/binding particle complexes, concentrations of said binding particles and labeled analyte particles, channel diffusion dimensions, length of channel (1) to detection zone, and binding kinetics of said analyte and binding particles.

5. The device of claim 1 also comprising a reference stream inlet into said laminar flow channel constructed and arranged such that a reference stream entering the laminar flow channel through said inlet can flow in laminar flow contact with said diffusion stream.

6. The device of claim 1 also comprising a reference stream comprising a known concentration of labeled analyte particles and a known concentration of unlabeled analyte particles in said laminar flow channel.

7. The device of claim 1 also comprising an inert separation stream inlet constructed and arranged such that an inert separation stream entering the laminar flow channel therethrough can flow in laminar flow contact with and between said analyte and diffusion streams.

8. The device of claim 1 also comprising an inert separation stream flowing in said laminar flow channel between said analyte and diffusion streams.

9. A device for determining the presence or concentration of sample analyte particles in a medium comprising:

(a) a laminar flow channel for contacting a first medium containing analyte particles with a second medium containing binding particles for binding to said analyte particles in adjacent laminar flow;

(b) wherein in operation said analyte particles in said first medium diffuse into said second medium or said binding particles in said second medium diffuse into the first medium containing said analyte particles; and (c) means for detecting the presence or concentration of diffused particles.

10. The device of claim 9 wherein at least one of said analyte particles or said binding particles is labeled.

11. The device of claim 9 wherein said first medium contains a known quantity of labeled analyte particles.

12. A device for detecting the presence of at least first and second analyte particles in a first fluid comprising:

(a) first inlet means for conducting a first fluid comprising said first and second analyte particles into a laminar flow channel;

(b) second inlet means for conducting a second fluid comprising first and second binding particles for said first and second analyte particles, respectively, into said laminar flow channel;

(c) a laminar flow channel in fluid communication with said first and second inlet means, comprising said first and second fluids in adjacent laminar flow, said flow channel having a length sufficient to allow said first analyte particles to diffuse into said second fluid and bind with said first binding particles to form first complexes; and to allow said second analyte particles to diffuse into said second fluid and bind with said second binding particles to form second complexes; and (d) means for detecting the presence of said first and second complexes.

13. The device of claim 12 wherein said first and second complexes have detectably different diffusion coefficients.

14. The device of claim 12 wherein said laminar flow channel displays detectably different diffusion profiles for of said first and second complexes.

15. The device of claim 12 wherein said first and second complexes are labeled with detectably different labels.

16. The device of claim 12 wherein said first and second complexes are not labeled with detectably different labels.

17. The device of claim 12 comprising outlet means spaced along said laminar flow channel for conducting a stream comprising said first complexes from said channel as a first outlet stream.

18. The device of claim 17 comprising outlet means spaced along said laminar flow channel for conducting a stream comprising said first and second complexes from said channel as a second outlet stream.

19. The device of claim 18 comprising means for detecting the presence of said second analyte particles in said second outlet stream.

20. The device of claim 17 comprising means for detecting the presence of said first analyte particles in said first outlet stream.

21. A device for separating first and second analyte particles of similar size contained in a first fluid, in a diffusion separator, said device comprising:

(a) a flow channel comprising a second fluid containing at least first and second binding particles for said first and second analyte particles, respectively, said first binding particles having a higher diffusion coefficient than said second binding particles, with said first analyte particles diffusing into said second fluid to bind with said first binding particles to form first complexes and said second analyte particles diffusing into said second fluid to bind with said second binding particles to form second complexes;

(b) a first inlet into said channel on a first side of said channel, said first inlet containing said first fluid;

(c) a second inlet on the second side of said flow channel containing an acceptor stream;

(d) a first outlet on the second side of said flow channel downstream from said second inlet containing a stream predominantly comprising said first complexes; and (e) a second outlet on the second side of said flow channel downstream from said first outlet containing a stream containing said first and second complexes.

22. The device of claim 21 also comprising a third outlet on the first side of said flow channel.

23. The device of claim 21 also comprising an additional diffusion separator connected to said first outlet.

24. The device of claim 21 also comprising an additional diffusion separator connected to said second outlet.

* * * * *